US009782517B2

(12) United States Patent
Pollock et al.

(10) Patent No.: US 9,782,517 B2
(45) Date of Patent: *Oct. 10, 2017

(54) CROSSLINKED HYALURONIC ACID-COLLAGEN GELS FOR IMPROVING TISSUE GRAFT VIABILITY AND SOFT TISSUE AUGMENTATION

(71) Applicant: Allergan, Inc., Irvine, CA (US)

(72) Inventors: Jacob F. Pollock, Honolulu, HI (US); Lauren E. Kokai, Santa Barbara, CA (US); Cunqi Cui, Goleta, CA (US); Xiaojie Yu, Irvine, CA (US); Dennis E. Van Epps, Goleta, CA (US); Darin J. Messina, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/494,991

(22) Filed: Apr. 24, 2017

(65) Prior Publication Data

US 2017/0224873 A1 Aug. 10, 2017

Related U.S. Application Data

(63) Continuation of application No. 14/535,033, filed on Nov. 6, 2014, now Pat. No. 9,662,422, which is a continuation of application No. 13/740,712, filed on Jan. 14, 2013, now abandoned, which is a continuation-in-part of application No. 13/728,855, filed on Dec. 27, 2012, now abandoned, which is a continuation-in-part of application No. 13/667,581, filed on Nov. 2, 2012, now abandoned, which is a continuation-in-part of application No. 13/605,565, filed on Sep. 6, 2012, now abandoned, which is a continuation-in-part of application No. 13/603,213, filed on Sep. 4, 2012, now abandoned.

(60) Provisional application No. 61/586,589, filed on Jan. 13, 2012, provisional application No. 61/580,971, filed on Dec. 28, 2011, provisional application No. 61/555,970, filed on Nov. 4, 2011, provisional application No. 61/531,533, filed on Sep. 6, 2011.

(51) Int. Cl.
| | |
|---|---|
| *A61L 27/52* | (2006.01) |
| *A61L 27/24* | (2006.01) |
| *A61K 8/65* | (2006.01) |
| *A61L 27/36* | (2006.01) |
| *A61L 27/38* | (2006.01) |
| *A61L 27/54* | (2006.01) |
| *A61L 27/58* | (2006.01) |
| *A61L 27/26* | (2006.01) |

(52) U.S. Cl.
CPC ............... *A61L 27/52* (2013.01); *A61L 27/26* (2013.01); *A61L 27/3604* (2013.01); *A61L 27/3804* (2013.01); *A61L 27/54* (2013.01); *A61L 27/58* (2013.01); *A61L 2300/412* (2013.01); *A61L 2300/64* (2013.01); *A61L 2400/06* (2013.01); *A61L 2430/34* (2013.01)

(58) Field of Classification Search
CPC .. A61L 27/52; A61L 27/3604; A61L 27/3804; A61L 27/54; A61L 27/58; A61L 27/26; A61L 2300/64; A61L 2300/412; A61L 2430/34; A61L 2400/06

See application file for complete search history.

(56) References Cited

U.S. PATENT DOCUMENTS

| | | | |
|---|---|---|---|
| 5,972,385 | A | 10/1999 | Liu et al. |
| 6,129,761 | A | 10/2000 | Hubbell |
| 6,991,652 | B2 | 1/2006 | Burg |
| 7,129,209 | B2 | 10/2006 | Rhee |
| 7,316,822 | B2 | 1/2008 | Binette |
| 7,767,452 | B2 | 8/2010 | Kleinsek |
| 7,799,767 | B2 | 9/2010 | Lamberti et al. |
| 7,875,296 | B2 | 1/2011 | Binette |
| 8,053,423 | B2 | 11/2011 | Lamberti et al. |
| 8,137,702 | B2 | 3/2012 | Binette et al. |
| 8,153,591 | B2 | 4/2012 | Masters et al. |
| 8,246,947 | B2 | 8/2012 | Hedrick et al. |
| 8,691,279 | B2 | 4/2014 | Guillen |
| 2005/0025755 | A1 | 2/2005 | Hedrick et al. |
| 2005/0186673 | A1 | 8/2005 | Geistlich et al. |
| 2006/0029578 | A1 | 2/2006 | Hoemann et al. |
| 2006/0189516 | A1 | 8/2006 | Yang et al. |
| 2007/0003525 | A1 | 1/2007 | Moehlenbruck ....... A61K 35/30 424/93.7 |
| 2007/0104692 | A1 | 5/2007 | Quijano et al. |
| 2007/0104693 | A1 | 5/2007 | Quijano et al. |

(Continued)

FOREIGN PATENT DOCUMENTS

| | | | |
|---|---|---|---|
| EP | 1532991 A1 | 5/2005 | |
| JP | 2002/080501 A | 3/2002 | ............. C08B 37/08 |
| KR | 20130018518 | 2/2013 | |
| WO | 0046252 A1 | 8/2000 | |
| WO | 2005052035 A1 | 6/2005 | |

(Continued)

OTHER PUBLICATIONS

Tomihata, Kenji et al., Crosslinking of Hyaluronic Acid with Water-Soluable Carbodiimide, J. Biomed Mater Res., Feb. 1997, pp. 243-251, vol. 37(2).

(Continued)

*Primary Examiner* — Julie Ha
*Assistant Examiner* — Li Ni Komatsu
(74) *Attorney, Agent, or Firm* — Barbara C. Potts

(57) ABSTRACT

Hydrogels comprising a macromolecular matrix and water may be used to augment soft tissue of a human being, promote or support cell or tissue viability or proliferation, create space in tissue, and for other purposes. A macromolecular matrix may comprise a hyaluronic acid component crosslinked to a collagen component.

43 Claims, 5 Drawing Sheets

(56) References Cited

U.S. PATENT DOCUMENTS

| | | |
|---|---|---|
| 2008/0300681 A1 | 12/2008 | Rigotti et al. |
| 2009/0093755 A1 | 4/2009 | Schroeder ............... A61L 27/26 604/57 |
| 2009/0098177 A1 | 4/2009 | Werkmeister et al. |
| 2009/0123547 A1 | 5/2009 | Hill et al. |
| 2009/0124552 A1 | 5/2009 | Hill et al. |
| 2009/0162415 A1 | 6/2009 | Huang et al. |
| 2009/0181104 A1 | 7/2009 | Rigotti et al. |
| 2009/0317376 A1 | 12/2009 | Zukowska et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0247651 A1 | 9/2010 | Kestler |
| 2010/0249924 A1 | 9/2010 | Powell et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0052695 A1 | 3/2011 | Jiang et al. |
| 2011/0070281 A1 | 3/2011 | Altman |
| 2011/0097381 A1 | 4/2011 | Binette |
| 2011/0104800 A1 | 5/2011 | Kensy et al. |
| 2011/0111031 A1 | 5/2011 | Jiang et al. |
| 2011/0150823 A1 | 6/2011 | Huang |
| 2011/0150846 A1 | 6/2011 | Van Epps |
| 2011/0183001 A1 | 7/2011 | Rosson et al. |
| 2011/0183406 A1 | 7/2011 | Kensy |
| 2011/0189292 A1 | 8/2011 | Lebreton et al. |
| 2011/0194945 A1 | 8/2011 | Kensy et al. |
| 2011/0229574 A1 | 9/2011 | Guillen et al. |
| 2011/0295238 A1 | 12/2011 | Kensy et al. |
| 2012/0010146 A1 | 1/2012 | Han et al. |
| 2012/0045420 A1 | 2/2012 | Van Epps et al. |
| 2012/0076868 A1 | 3/2012 | Lamberti et al. |
| 2012/0100611 A1 | 4/2012 | Kensy et al. |
| 2012/0156265 A1 | 6/2012 | Binette et al. |
| 2012/0164116 A1 | 6/2012 | Van Epps |
| 2012/0165935 A1 | 6/2012 | Van Epps |
| 2012/0171265 A1 | 7/2012 | Altman et al. |
| 2012/0172317 A1 | 7/2012 | Altman et al. |
| 2012/0172985 A1 | 7/2012 | Altman et al. |
| 2012/0207837 A1 | 8/2012 | Powell et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0244943 A1 | 9/2013 | Yu et al. |
| 2014/0227235 A1 | 8/2014 | Kim et al. |

FOREIGN PATENT DOCUMENTS

| | | | |
|---|---|---|---|
| WO | 2006015490 A1 | 2/2006 | |
| WO | 2008063569 | 5/2008 | |
| WO | 2008-098019 A3 | 8/2008 | |
| WO | 2008148071 | 12/2008 | |
| WO | 2009003135 | 12/2008 | |
| WO | 2009026158 A3 | 2/2009 | |
| WO | WO 2010/003104 A2 | 1/2010 | ............ A61L 27/58 |
| WO | 2010026299 | 3/2010 | |
| WO | 2011072399 | 6/2011 | |
| WO | 2011-119468 A1 | 9/2011 | |
| WO | 2013015579 A2 | 1/2013 | |
| WO | 2013-036568 A1 | 3/2013 | |
| WO | 2013-067293 A1 | 5/2013 | |

OTHER PUBLICATIONS

Van Der Rest et al., "Collagen family of proteins", The FASEB Journal, vol. 5, Oct. 1991, pp. 2814-2823.

Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.

International Pharmacopoeia Fourth Edition, Methods of Analysis: 5. Pharmaceutical technical procedures: 5.8 Methods of sterilization, http://apps.who.int/phint/en/d/Jb/7.5.9.html, Sep. 25, 2013.

Sterilization-microbiology, http://www.ask.com/wiki/Sterilization_(microbiology), pp. 1-9, Sep. 25, 2013.

Crosslinking Technical Handbook, Thermo Scientific, pp. 1-48, published Apr. 2009.

Kreisel et al., "Cell-delivery therapeutics for adipose tissue regeneration", Advanced Drug Delivery Reviews 62 (2010) 798-813.

Etienne et al, Soft Tissue Augmentation Using Silk Gels: An In Vitro and In Vivo Study, J. Periodontol, 2009, 80, pp. 1852-1858.

Altman et al., "Adhesion, migration and mechanics of human adipose-tissue-derived stem cells on silk fibroin-chitosan matrix", Acta Biomaterialia 6 (2010) 1388-1397.

Park et al., "Biological Characterization of EDC-crosslinked Collagen-Hyaluronic Acid Matrix in Dermal Tissue Restoration", Biomaterials 24 (2003) 1631-1641.

Park et al., "Characterization of Porous Collagen/Hyaluronic Acid Scaffold Modified by 1-ethyl-3-(3-dimethylaminopropyl) carbodiimide cross-linking", Biomaterials 23 (2002): 1205-1212.

Taguchi et al., "An improved method to prepare hyaluronic acid and type II collagen composite matrices", Journal of Biomedical Materials Research (2002), 61(2), 330-336.

Greco et al., "Hyaluronic Acid Stimulates Human Fibroblast Proliferation Within a Collagen Matrix", J. Cell. Physiol. 177 (3):465-473, 1998.

Calderon et al., "Type II Collagen-Hyaluronan Hydrogel—A Step Towards a Scaffold for Intervertebral Disc Tissue Engineering", European Cells and Materials, vol. 20, pp. 134-148, 2010.

Doillon et al., "Fibroblast growth on a porous collagen sponge containing hyaluronic acid and fibronectin", Biomaterials 8 (1987) 195-200.

Davidenko et al., "Collagen-hyaluronic acid scaffolds for adipose tissue engineering", Acta Biomaterialia 6 (2010) 3957-3968.

Tissue of the Human Body, from http://www.mhhe.com/biosci/ap/histology_mh/tismodov.html, pp. 1-2, accessed Jun. 9, 2014.

Machine translation of JP 2002/080501 A, pp. 1-8, accessed Sep. 19, 2013.

Wang et al, Development of hyaluronic acid-based scaffolds for brain tissue engineering, Acta Biomaterialia, 2009, 5, pp. 2371-2384.

Definition of space, from http://www.merriam-webster.com/dictionary/space, pp. 1-5, accessed Jan. 10, 2014.

Vialle-Presles et al, Immunohistochemical study of the biological fate of a subcutaneous bovine collagen implant in rat, Histochemistry, 1989, 91, pp. 177-184.

Mast et al, Hyaluronic acid degradation products induce neovascularization and fibroplasia in fetal rabbit wounds, Wound Repair and Regeneration, 1995, 3, pp. 66-72.

Kablik et al, Comparative Physical Properties of Hyaluronic Acid Dermal Fillers, Dermatol Surg, 2009, 35, pp. 302-312.

Z-Hun Kim et al., A Composite Dermal Filler Comprising Cross-Linked Hyaluronic Acid and Human Collagen for Tissue Reconstrution, J. Microbiol. Biotechnol., 2015, pp. 399-406, 25 (3), The Korean Society for Microbiology & Biotechnology.

HA Col(1)16:8

HA Col(1)12:12

CROSSLINKED HYALURONIC ACID-COLLAGEN GELS FOR IMPROVING TISSUE GRAFT VIABILITY AND SOFT TISSUE AUGMENTATION

CROSS-REFERENCE TO RELATED APPLICATIONS

This application claims the benefit of U.S. Provisional Patent Application No. 61/586,589, filed Jan. 13, 2012, and is a continuation of U.S. patent application Ser. No. 14/535,033 filed on Nov. 6, 2014, which granted as U.S. Pat. No. 9,662,422 on May 30, 2017, which is a continuation of U.S. patent application Ser. No. 13/740,712 filed on Jan. 14, 2013 and abandoned on Mar. 16, 2015, which is a continuation-in-part of U.S. patent application Ser. No. 13/728,855, filed Dec. 27, 2012 and abandoned on Sep. 12, 2014, which is a continuation-in-part of U.S. patent application Ser. No. 13/667,581, filed on Nov. 2, 2012 and abandoned on Mar. 14, 2016, which is a continuation-in-part of U.S. patent application Ser. No. 13/605,565, filed on Sep. 6, 2012 and abandoned on Jul. 18, 2014, which is a continuation-in-part of U.S. patent application Ser. No. 13/603,213 filed on Sep. 4, 2012 and abandoned on Jan. 21, 2015; U.S. patent application Ser. No. 13/728,855 claims the benefit of U.S. Provisional Patent Application No. 61/580,971, filed Dec. 28, 2011; U.S. patent application Ser. No. 13/667,581 claims the benefit of U.S. Provisional Patent Application No. 61/555,970, filed Nov. 4, 2011; U.S. patent application Ser. No. 13/605,565 claims the benefit of U.S. Provisional Patent Application No. 61/531,533, filed Sep. 6, 2011; and U.S. patent application Ser. No. 13/603,213 claims the benefit of U.S. Provisional Patent No. 61/531,533, filed Sep. 6, 2011; the entire content of each of these documents is incorporated herein by this specific reference.

BACKGROUND

Hyaluronic acid and collagen are key structural components of human tissues. These biopolymers have been widely used to construct tissue engineering scaffolds and materials for cell culturing and regenerative medicine.

Autologous fat transfer (AFT), also known as fat grafting, is a process by which fat is harvested from one part of a human body and injected into another part of the same person's body where additional bulk may be needed for cosmetic and/or aesthetic purposes. Clinical applications for autologous fat transfer are expanding rapidly with recent reported use in breast reconstruction and augmentation, buttock enhancement, treatment of congenital tissue defects, facial reconstruction, and skin rejuvenation. Although this is a very attractive approach and there is an increased trend in replacement of soft tissue volume with AFT, typical survival rates of grafted fat may be poor and overall results may not be satisfactory to a patient.

The present invention addresses these and other shortcomings in the field of cosmetic and reconstructive medicine and procedures.

SUMMARY

Hydrogels and hydrogel compositions have been developed that are useful for soft tissue augmentation procedures, including tissue reconstruction procedures. These hydrogels and hydrogel compositions may promote and/or support the survival or growth of living cells and other components of tissues.

In one aspect, a soft tissue augmentation product is provided which can be injected or introduced into tissue along with a cellular component. The product may comprise a forming component comprising a hydrogel described herein, the hydrogel having a form suitable for augmenting human soft tissue by introducing, for example, by injection or implantation, the forming component into the human tissue. In some embodiments, the hydrogel itself contains or includes a cellular material, for example, living tissue or living cells, and a component hyaluronic acid and collagen. The product may further comprise a label including instructions for such injecting or implanting the forming component. In addition, the product may, in some embodiments, include a syringe or other device for facilitating the introducing of the forming component.

Typically, in accordance with one aspect of the invention, a hydrogel or a hydrogel composition may comprise water, and a crosslinked macromolecular matrix. The matrix may be in a form suitable for mixing or combining with living cells or tissue prior to introduction of the matrix into the portion or anatomical feature being augmented. In some embodiments, the matrix comprises a hyaluronic acid component; and a collagen component. In a more specific aspect of the invention, the hyaluronic acid is crosslinked to the collagen, for example, by a crosslinking component. In one especially advantageous embodiment, at least a portion of the crosslink units of the crosslinking component comprises an ester bond or an amide bond.

In another aspect of the invention, methods of augmenting soft tissue of a human being are provided which comprise injecting or implanting a hydrogel composition described herein into a soft tissue of the human being to thereby augment the soft tissue. In some embodiments, the method includes combining, or mixing the hydrogel composition with living cells or tissue that have been explanted from the patient. The composition may be especially effective in enhancing cell proliferation and/or supporting cell viability when reintroduced, for example, into a breast of a patient. Thus, the method in these instances may be useful in conjunction with fat grafting procedures.

Other aspects of the invention are directed toward methods of promoting or supporting cell proliferation or survival, for example, in fat grafting procedures or other augmentation or reconstructive procedures. For example, the methods may include contacting hydrogel compositions described herein with cellular materials, cells and/or tissue, for example, prior to injecting the compositions into the body.

In yet other aspects of the invention, methods are provides for preparing a space in human or animal tissue, for example, for later receipt of a fat graft or implant, the method comprising injecting a hydrogel composition described herein into the tissue, and allowing growth or proliferation of tissue while the composition degrades over time.

DETAILED DESCRIPTION

Figure 1A:
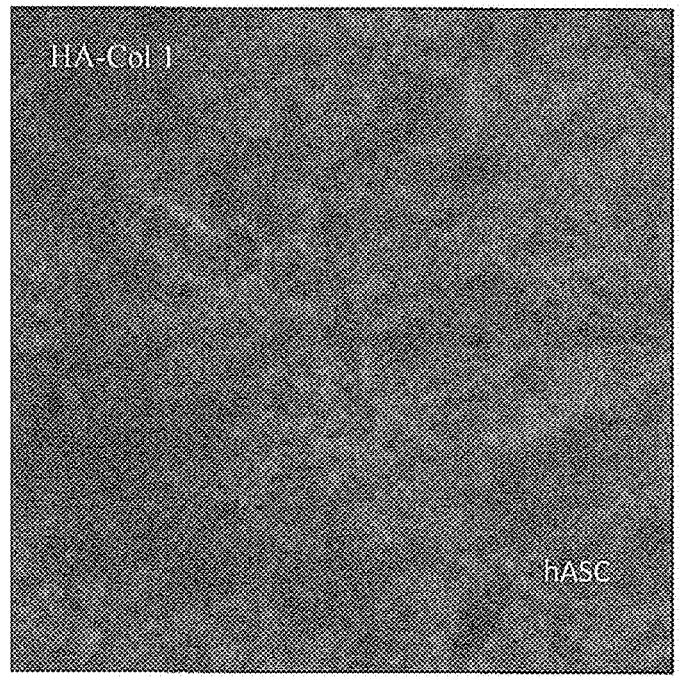
FIGS. 1A and 1B are bright field micrographs of the attachment of cells on a hyaluronic acid-collagen(I) hydrogel of Example 9 (18 hrs) (FIG. 1A) as compared to a hyaluronic acid control (FIG. 1B).

Hydrogels described herein may be used to augment soft tissue of a human being. For example, a hydrogel or a hydrogel composition may be injected or implanted a hydrogel composition into a soft tissue of the human being to thereby augment the soft tissue. In some embodiments, a forming component may comprise a hydrogel or a hydrogel having a form suitable for augmenting human soft tissue by injecting or implanting the forming component into the human tissue.

A forming component may be any object or substance with a form that is suitable for a particular augmentation need. For example, a forming component may have a viscosity, firmness, and/or other physical properties such that, when injected or implanted into a soft tissue to augment the tissue, the newly augmented portion of the tissue is reasonably similar to the natural tissue. If a forming component is to be injected, it may be in a form that is suitable for injection. For example, the viscosity may be low enough so that injection through a needle is possible. If a forming component is to be implanted, in some circumstances it may be desirable for the forming component to be solid or sufficiently viscous so as to maintain its shape during implantation.

Some augmentation products may include a label comprising instructions to inject or implant the forming component into the human tissue.

Hydrogels described herein may also be used to enhance, promote or support cell proliferation or survival. Some embodiments include a method comprising contacting a hydrogel or a hydrogel composition with a cell or cells.

A hydrogel or a hydrogel composition that contacts one or more cells may promote or support survival of the cells, including adipocytes, adipose-derived stem cells, stromal vascular fraction cells, or a combination thereof. For example, a hydrogel or a hydrogel composition described herein may promote or support cell survival to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition described herein may promote or support cell survival to a greater extent than a hydrogel composition comprising water and hyaluronic acid at a concentration of about 24 mg/mL or about 16 mg/mL. Contact between a hydrogel or a hydrogel composition described herein and cells may promote or support cell survival in vivo to a greater extent than a hydrogel composition that is substantially identical except that the hyaluronic acid component and the collagen component are not crosslinked. In some embodiments, a hydrogel or a hydrogel composition may promote or support cell survival about as well as, or better than, tissue culture polystyrene.

A hydrogel composition disclosed herein may enhance survival of one or more cells. In one embodiment, a hydrogel composition disclosed herein enhances survival of one or more cells as compared to cells alone. In aspects of this embodiment, a hydrogel composition disclosed herein enhances survival of one or more cells by at least about 50% at least about 100%, at least about 150%, at least about 200%, at least 250%, at least about 300%, at least about 350%, at least about 400%, at least about 450%, or at least about 500% as compared to cells alone. In aspects of this embodiment, a hydrogel composition disclosed herein enhances survival of one or more cells by about 50% to about 250%, about 50% to about 500%, about 50% to about 1000%, about 100% to about 300%, about 100% to about 500%, about 150% to about 400%, about 150% to about 500%, or about 200% to about 500%, as compared to cells alone.

In some embodiments, a hydrogel composition disclosed herein enhances survival of one or more cells as compared to cells with a hydrogel composition that is substantially identical except that the hyaluronic acid component and the collagen component are not crosslinked. In aspects of this embodiment, a hydrogel composition disclosed herein enhances survival of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the hyaluronic acid component and the collagen component are not crosslinked. In aspects of this embodiment, a hydrogel composition disclosed herein enhances survival of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL and water.

In yet another embodiment, a hydrogel composition disclosed herein enhances survival of one or more cells as compared to cells with a hydrogel composition that is substantially identical except that the collagen component is absent. In aspects of this embodiment, a hydrogel composition disclosed herein enhances survival of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the collagen component is absent. In aspects of this embodiment, a hydrogel composition disclosed herein enhances survival of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL and water.

A hydrogel or a hydrogel composition that contacts one or more cells may promote or support proliferation of cells, such as regenerative cells, stem cells, progenitor cells, precursor cells, adipose-derived stem cells, stromal vascular fraction cells, etc. A hydrogel or a hydrogel composition described herein may also promote or support cell proliferation to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition described herein may promote or support cell proliferation to a greater extent than a hydrogel composition comprising water and hyaluronic acid at a concentration of about 24 mg/mL or about 16 mg/mL. Contact between a hydrogel or a hydrogel composition described herein and cells may promote or support cell proliferation to a greater extent than a hydrogel composition that is substantially identical except that the hyaluronic acid component and the collagen component are not crosslinked. In some embodiments, a hydrogel or a hydrogel composition may promote or support cell proliferation about as well as, or better than, tissue culture polystyrene.

A hydrogel composition disclosed herein may enhance proliferation of one or more cells. In one embodiment, a hydrogel composition disclosed herein enhances proliferation of one or more cells as compared to cells alone. In aspects of this embodiment, a hydrogel composition disclosed herein enhances proliferation of one or more cells by at least about 50% at least about 100%, at least about 150%, at least about 200%, at least 250%, at least about 300%, at least about 350%, at least about 400%, at least about 450%, or at least about 500 as compared to cells alone. In aspects of this embodiment, a hydrogel composition disclosed herein enhances proliferation of one or more cells by about 50% to about 250%, about 50% to about 500%, about 50% to about 1000%, about 100% to about 300%, about 100% to about 500%, about 150% to about 400%, about 150% to about 500%, or about 200% to about 500%, as compared to cells alone.

In another embodiment, a hydrogel composition disclosed herein enhances proliferation of one or more cells as compared to cells with a hydrogel composition that is substantially identical except that the hyaluronic acid component and the collagen component are not crosslinked. In aspects of this embodiment, a hydrogel composition disclosed herein enhances proliferation of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the hyaluronic acid component and the collagen component are not crosslinked. In aspects of this embodiment, a hydrogel composition disclosed herein enhances proliferation of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In yet another embodiment, a hydrogel composition disclosed herein enhances proliferation of one or more cells as compared to cells with a hydrogel composition that is substantially identical except that the collagen component is absent. In aspects of this embodiment, a hydrogel composition disclosed herein enhances proliferation of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the collagen component is absent. In aspects of this embodiment, a hydrogel composition disclosed herein enhances proliferation of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

A hydrogel or a hydrogel composition of the present disclosure may include a cellular component, for example, components of human adipose tissue, for example, adipose-derived stem cells, stromal vascular fraction cells, etc.

When injected or implanted in vivo, a hydrogel or a hydrogel composition may promote cell and/or tissue growth, including growth into the implant material. For example, a hydrogel or hydrogel composition may stimulate angiogenesis, neovascularization, adipogenesis, collagenesis, cell infiltration, tissue integration, and the like in vivo. In some embodiments, a hydrogel or a hydrogel composition may promote this type of growth or activity to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition may promote this type of growth or activity to a greater extent than a hydrogel composition comprising water and hyaluronic acid at a concentration of about 24 mg/mL or about 16 mg/mL. In some embodiments, a hydrogel or a hydrogel composition may promote this type of growth or activity to a greater extent than a hydrogel composition that is substantially identical except that the hyaluronic acid component and the collagen component are not crosslinked.

Once injected or implanted into a soft tissue, a hydrogel composition disclosed herein may stimulate angiogenesis, neovascularization, adipogenesis, and/or collagenesis. In an embodiment, a hydrogel composition disclosed herein stimulates angiogenesis, neovascularization, adipogenesis, and/or collagenesis to a greater extent as compared to a hydrogel composition that is substantially identical except that the hyaluronic acid component and the collagen component are not crosslinked. In aspects of this embodiment, a hydrogel composition disclosed herein angiogenesis, neovascularization, adipogenesis, and/or collagenesis by at least about 50% at least about 100%, at least about 150%, at least about 200%, at least 250%, at least about 300%, at least about 350%, at least about 400%, at least about 450%, at least about 500%, at least about 750%, or at least about 1000% as compared to a hydrogel composition that is substantially identical except that the hyaluronic acid component and the collagen component are not crosslinked. In aspects of this embodiment, a hydrogel composition disclosed herein angiogenesis, neovascularization, adipogenesis, and/or collagenesis by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In another embodiment, a hydrogel composition disclosed herein stimulates angiogenesis, neovascularization, adipogenesis, and/or collagenesis to a greater extent as compared to adipose tissue with a hydrogel composition that is substantially identical except that the collagen component is absent. In aspects of this embodiment, a hydrogel composition disclosed herein angiogenesis, neovascularization, adipogenesis, and/or collagenesis by at least about 50% at least about 100%, at least about 150%, at least about 200%, at least 250%, at least about 300%, at least about 350%, at least about 400%, at least about 450%, at least about 500%, at least about 750%, or at least about 1000% as compared to a hydrogel composition that is substantially identical except that the collagen component is absent. In aspects of this embodiment, a hydrogel composition disclosed herein angiogenesis, neovascularization, adipogenesis, and/or collagenesis by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

Once injected or implanted into a soft tissue, a hydrogel composition disclosed herein may show infiltration and/or tissue integration of cells from the soft tissue. In an embodiment, a hydrogel composition disclosed herein shows cell infiltration and/or tissue integration from the soft tissue to a greater extent as compared to a hydrogel composition that is substantially identical except that the hyaluronic acid component and the collagen component are not crosslinked. In aspects of this embodiment, a hydrogel composition disclosed herein shows enhanced cell infiltration and/or tissue integration by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the hyaluronic acid component and the collagen component are not crosslinked. In aspects of this embodiment, a hydrogel composition disclosed herein shows enhanced cell infiltration and/or tissue integration by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In another embodiment, a hydrogel composition disclosed herein may show cell infiltration and/or tissue integration from the soft tissue to a greater extent as compared to a hydrogel composition that is substantially identical except that the collagen component is absent. In aspects of this embodiment, a hydrogel composition disclosed herein shows enhanced cell infiltration and/or tissue integration by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the collagen component is absent. In aspects of this embodiment, a hydrogel composition disclosed herein shows enhanced cell infiltration and/or tissue integration by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

In some methods, hydrogel or a hydrogel composition may be mixed with tissue, for example, adipose tissue or fat tissue from the human being, such as human lipoaspirate, or from fat from another human being or an animal. The ratio of hydrogel to fat in such a mixture may vary to provide the desired results. The fat:hydrogel ratio is the weight of the fat divided by the weight of hydrogel. For example, if 1 gram of fat is mixed with 10 grams of hydrogel, the fat:hydrogel weight ratio is 0.1. In some embodiments, the fat tissue and the hydrogel may have a fat:hydrogel weight ratio of about 0.1 up to about 10. All other fat:hydrogel weight ratios falling within this range are also contemplated and considered to be within the scope of the present invention. For example, the weight ratio may be about 0.5 up to about 7, for example, about 1 up to about 5. In some embodiments, the fat:hydrogel weight ratio is about 1 to about 3, for example, about 1, about 2, or about 3.

A combination or mixture of human fat tissue and hydrogel composition may then be injected or implanted into soft tissue of a human being, for augmenting the breast for example. This may help to improve the survival time of grafted fat in autologous and other fat transfer procedures. It may also help to improve volume retention, reduce the variability in retained fat graft volume, and/or reduce inflammation as compared to injecting fat tissue alone.

A hydrogel composition disclosed herein may show improved volume retention after injection or implantation into a soft tissue. In an embodiment, a hydrogel composition disclosed herein shows improved volume retention after injection or implantation into a soft tissue as compared to a hydrogel composition that is substantially identical except that the hyaluronic acid component and the collagen component are not crosslinked. In aspects of this embodiment, a hydrogel composition disclosed herein shows improved volume retention after injection or implantation into a soft tissue by at least about 5% at least about 10%, at least about 15%, at least about 20%, at least about 25%, at least about 30%, at least about 35%, at least about 40%, at least about 45%, or at least about 50% as compared to a hydrogel composition that is substantially identical except that the hyaluronic acid component and the collagen component are not crosslinked. In aspects of this embodiment, a hydrogel composition disclosed herein shows improved volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In another embodiment, a hydrogel composition disclosed herein shows improved volume retention after injection or implantation into a soft tissue as compared to a hydrogel composition that is substantially identical except that the collagen component is absent. In aspects of this embodiment, a hydrogel composition disclosed herein shows improved volume retention after injection or implantation into a soft tissue by at least about 5% at least about 10%, at least about 15%, at least about 20%, at least about 25%, at least about 30%, at least about 35%, at least about 40%, at least about 45%, or at least about 50% as compared to a hydrogel composition that is substantially identical except that the collagen component is absent. In aspects of this embodiment, a hydrogel composition disclosed herein shows improved volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

A hydrogel composition disclosed herein may show decreased variability in volume retention after injection or implantation into a soft tissue. In an embodiment, a hydrogel composition disclosed herein shows decreased variability in volume retention after injection or implantation into a soft tissue as compared to a hydrogel composition that is substantially identical except that the hyaluronic acid component and the collagen component are not crosslinked. In aspects of this embodiment, a hydrogel composition disclosed herein shows decreased variability in volume retention after injection or implantation into a soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the hyaluronic acid component and the collagen component are not crosslinked. In aspects of this embodiment, a hydrogel composition disclosed herein shows decreased variability in volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In another embodiment, a hydrogel composition disclosed herein shows decreased variability in volume retention after injection or implantation into a soft tissue as compared to a hydrogel composition that is substantially identical except that the collagen component is absent. In aspects of this embodiment, a hydrogel composition disclosed herein shows decreased variability in volume retention after injection or implantation into a soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the collagen component is absent. In aspects of this embodiment, a hydrogel composition disclosed herein shows decreased variability in volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

Once injected or implanted into a soft tissue, a hydrogel composition disclosed herein may reduce inflammation of the soft tissue. In an embodiment, a hydrogel composition disclosed herein reduces inflammation of the soft tissue as compared to a hydrogel composition that is substantially identical except that the hyaluronic acid component and the collagen component are not crosslinked. In aspects of this embodiment, a hydrogel composition disclosed herein reduces inflammation of the soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the hyaluronic acid component and the collagen component are not crosslinked. In aspects of this embodiment, a hydrogel composition disclosed herein reduces inflammation of the soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In another embodiment, a hydrogel composition disclosed herein reduces inflammation of the soft tissue as compared to a hydrogel composition that is substantially identical except that the collagen component is absent. In aspects of this embodiment, a hydrogel composition disclosed herein reduces inflammation of the soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the collagen component is absent. In aspects of this embodiment, a hydrogel composition disclosed herein reduces inflammation of the soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

A hydrogel or a hydrogel composition may have improved physical properties that may help to encourage cell survival or proliferation. In some embodiments, a hydrogel or a hydrogel composition may allow diffusion of adipose tissue-specific growth factors or pro-angiogenic growth factors to a greater extent than a hydrogel composition comprising hyaluronic acid at a concentration of about 24 mg/mL or about 16 mg/mL and water.

A hydrogel composition disclosed herein may show improved diffusion of adipose tissue-specific growth factors or pro-angiogenic growth factors. In an embodiment, a hydrogel composition disclosed herein shows diffusion of adipose tissue-specific growth factors or pro-angiogenic growth factors to a greater extent as compared to a hydrogel composition that is substantially identical except that the hyaluronic acid component and the collagen component are not crosslinked. In aspects of this embodiment, a hydrogel composition disclosed herein shows improved diffusion of adipose tissue-specific growth factors or pro-angiogenic growth factors by at least about 25% at least about 50%, at least about 75%, at least about 100%, at least 125%, at least about 150%, at least about 175%, at least about 200%, at least about 225%, or at least about 250% as compared to a hydrogel composition that is substantially identical except that the hyaluronic acid component and the collagen component are not crosslinked. In aspects of this embodiment, a hydrogel composition disclosed herein shows improved diffusion of adipose tissue-specific growth factors or pro-angiogenic growth factors by about 25% to about 100%, about 25% to about 150%, about 25% to about 250%, about 50% to about 100%, about 50% to about 150%, or about 50% to about 250% as compared to a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In another embodiment, a hydrogel composition disclosed herein shows diffusion of adipose tissue-specific growth factors or pro-angiogenic growth factors to a greater extent as compared to a hydrogel composition that is substantially identical except that the collagen component is absent. In aspects of this embodiment, a hydrogel composition disclosed herein shows improved diffusion of adipose tissue-specific growth factors or pro-angiogenic growth factors by at least about 25% at least about 50%, at least about 75%, at least about 100%, at least 125%, at least about 150%, at least about 175%, at least about 200%, at least about 225%, or at least about 250% as compared to a hydrogel composition that is substantially identical except that the collagen component is absent. In aspects of this embodiment, a hydrogel composition disclosed herein shows improved diffusion of adipose tissue-specific growth factors or pro-angiogenic growth factors by about 25% to about 100%, about 25% to about 150%, about 25% to about 250%, about 50% to about 100%, about 50% to about 150%, or about 50% to about 250% as compared to a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

A hydrogel or a hydrogel composition may be used to prepare a space in human or animal tissue. This may be done by injecting a hydrogel or a hydrogel composition into the tissue. After being injected, a hydrogel or a hydrogel composition may degrade over time, such as over a period of about 1 week to about 3 months or about 2 weeks to about 6 weeks, to thereby create the space in the tissue. This may create a fertile nutrient bed through stimulated angiogenesis, cellular ingrowth, secretion of tropic factors, as well as creating space. An anesthetic may also be injected into the tissue, such as before injection of a hydrogel or hydrogel composition, or as part of a hydrogel composition. This may help reduce the pain of injection and allow the procedure to be done as an outpatient procedure.

Once a hydrogel has degraded sufficiently to create a desired space, a human or animal fat composition may be injected into the space in the tissue. A fertile nutrient bed created as described above may help to improve overall fat graft retention as compared to injecting fat without preparing a space as described above.

Some embodiments include a packaged product comprising a device for facilitating introduction, for example, a syringe loaded with a hydrogel and a needle. A syringe may be fitted with a needle of any size that is appropriate for injecting the hydrogel into the soft tissue of interest, such as a needle with about a #25, about a #30, or a larger gauge.

A filler comprising a hydrogel may be suitable for injection if it can be injected into the soft tissue of interest without unreasonable difficulty, and includes fillers that can be dispensed from syringes having gauge as low as about #30 or about #25 under normal manual pressure with a smooth extrusion plateau.

Injection of a hydrogel may provide a soft tissue augmentation that mimics the natural components of the skin. A hydrogel may be injected intradermally or subcutaneously to augment soft tissue and to repair or correct congenital anomalies, acquired defects, or cosmetic defects. Examples of such conditions include congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, or post infectious) such as depressed scars, subcutaneous atrophy (e.g., secondary to discoid lupus erythematosus), keratotic lesions, enophthalmos in the unucleated eye (also superior sulcus syndrome), acne pitting of the face, linear scleroderma with subcutaneous atrophy, saddle-nose deformity, Romberg's disease, and unilateral vocal cord paralysis; and cosmetic defects such as glabellar frown lines, deep nasolabial creases, circum-oral geographical wrinkles, sunken cheeks, and mammary hypoplasia.

Hydrogels of crosslinked hyaluronic acid alone, collagen, and crosslinked collagen alone, such as those used in dermal fillers, do not actively promote cellular infiltration and tissue in-growth. Similarly, collagen simply blended into hyaluronic acid hydrogels does not promote tissue integration or de novo tissue generation. However, some hydrogels described herein do promote cellular migration into the hydrogels and tissue formation within the gels when implanted in vivo.

A hydrogel may comprise water and a crosslinked macromolecular matrix. Typically, a crosslinked molecular matrix may comprise a hyaluronic acid component and a collagen component, wherein the hyaluronic acid component is crosslinked to the collagen component by a crosslinking component. A crosslinking component may comprise a plurality of crosslink units, wherein at least a portion of the crosslink units comprise an ester bond or an amide bond.

A hydrogel or a hydrogel composition may be at least about 70%, about 93%, or about 96% water by weight, and may approach 100% water by weight. A crosslinked macromolecular matrix may be about 0.01% to about 30%, about 0.1% to about 7%, or about 0.2% to about 4% of the weight of a hydrogel or a hydrogel composition. A hyaluronic acid component may be about 0.005% to about 20%, about 0.1% to about 5% or about 0.2% to about 2.5% of the total weight of a hydrogel or a hydrogel composition. A collagen component may be about 0.01% to about 10%, about 0.03% to about 2%, or about 0.05% to about 1.2% of the total weight of a hydrogel or a hydrogel composition.

A crosslinked macromolecular matrix for a hydrogel may be synthesized by coupling a hyaluronic acid with a collagen using a coupling agent, such as a carbodiimide. In these hydrogels, hyaluronic acid may serve as a biocompatible water-binding component, providing bulk and isovolumetric degradation. Additionally, collagen may impart cell adhesion and signaling domains to promote cell attachment, migration, and other cell functions such as extra-cellular matrix deposition. The biopolymers form homogeneous hydrogels with tunable composition, swelling, and mechanical properties. Compositions can be made to be injectable for minimally invasive implantation through syringe and needle.

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups. Unless clearly indicated otherwise, reference to hyaluronic acid herein may include its fully protonated, or nonionic form as depicted below, as well as any anionic forms and salts of hyaluronic acid, such as sodium salts, potassium salts, lithium salts, magnesium salts, calcium salts, etc.

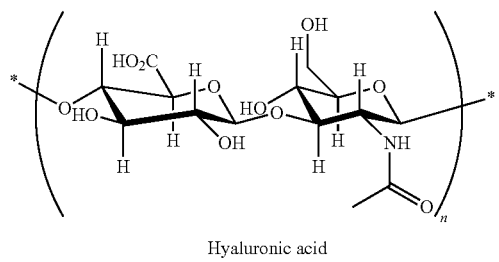

Hyaluronic acid

Collagen is a protein that forms fibrils and sheets that bear tensile loads. Collagen also has specific integrin-binding sites for cell adhesion and is known to promote cell attachment, migration, and proliferation. Collagen may be positively charged because of its high content of basic amino acid residues such as arginine, lysine, and hydroxylysine. Unless clearly indicated otherwise, reference to collagen herein may include uncharged collagen, as well as any cationic forms, anionic forms, or salts of collagen.

Because hyaluronic acid may be anionic and collagen may be cationic, the two macromolecules may form polyionic complexes in aqueous solution. A polyionic complex may be significantly less soluble in water than either hyaluronic acid or collagen, and thus may precipitate out of aqueous solution when the two macromolecules are together in a mixture. Furthermore, collagens are often soluble only at low pH and may precipitate from solution when brought to a pH amenable to carbodiimide coupling.

Under certain conditions, a hyaluronic acid and a collagen may be combined in an aqueous liquid in which both components are soluble. A hyaluronic acid and a collagen may then be crosslinked while both are dissolved in an aqueous solution to form a hydrogel. Reaction conditions such as the concentration of hyaluronic acid, the concentration of collagen, the pH of the solution, and salt concentration may be adjusted to help to prevent polyionic complex formation between anionic hyaluronic acid and cationic collagen. They may also help to prevent collagen microfibril formation, which results in precipitation from solution and may prevent crosslinking.

Some embodiments include a method of crosslinking hyaluronic acid and collagen. This method generally comprises a dissolution step which results in an aqueous pre-reaction solution. In a dissolution step, hyaluronic acid and collagen are dissolved in an aqueous solution that has a low pH and/or a salt to form an aqueous pre-reaction solution.

A hyaluronic acid-collagen crosslinking method further comprises an activation step. In an activation step, an aqueous pre-reaction solution is modified by at least adding a water soluble coupling agent and/or by increasing the pH of the solution. If needed, a salt may also be added to keep the hyaluronic acid and collagen in solution at the higher pH. Thus, a crosslinking reaction mixture comprises hyaluronic acid and collagen dissolved or dispersed in an aqueous medium, a water soluble coupling agent, and a salt, and has a higher pH than the aqueous pre-reaction solution from which it was derived. The crosslinking reaction mixture is allowed to react to thereby crosslink the hyaluronic acid and the collagen.

In some embodiments, the pH of the aqueous pre-reaction solution may be increased and a substantial amount of fiber formation may be allowed to occur in the solution before adding the water soluble coupling agent. In some embodiments, the water soluble coupling agent may be added to the aqueous pre-reaction solution before substantially any fiber formation occurs.

A crosslinking reaction mixture can react to form a crosslinked macromolecular matrix. Since reaction occurs in an aqueous solution, a crosslinked macromolecular matrix may be dispersed in an aqueous liquid in hydrogel form as it is formed by a crosslinking reaction. A crosslinked macromolecular matrix may be kept in hydrogel form because, in many instances, a crosslinked macromolecular matrix may be used in hydrogel form.

In some embodiments, an aqueous pre-reaction solution or a crosslinking reaction mixture may further comprise about 10% to about 90% of an organic solvent in which hyaluronic acid has poor solubility, such as ethanol, methanol, isopropanol, or the like.

After a crosslinking reaction has occurred, the crosslinked macromolecular matrix may be particulated or homogenized through a mesh. This may help to form an injectable slurry or hydrogel. A mesh used for particulating a crosslinked macromolecular matrix may have any suitable pore size depending upon the size of particles desired. In some embodiments, the mesh may have a pore size of about 10 microns to about 100 microns, about 50 microns to about 70 microns, or about 60 microns.

A hydrogel comprising a crosslinked molecular matrix may be treated by dialysis for sterilization or other purposes. Dialysis may be carried out by placing a semipermeable membrane between the hydrogel and another liquid so as to allow the hydrogel and the liquid to exchange molecules or salts that can pass through the membrane.

A dialysis membrane may have a molecular weight cutoff that may vary. For example, the cutoff may be about 5,000 daltons to about 100,000 daltons, about 10,000 daltons to about 30,000 daltons, or about 20,000 daltons.

The dialysis may be carried out against a buffer solution, meaning that the liquid on the other side of the membrane from the hydrogel may be a buffer solution. In some embodiments, the buffer solution may be a sterile phosphate buffer solution that may comprise phosphate buffer, potassium chloride, and/or sodium chloride. A sterile phosphate buffer solution may be substantially isosmotic with respect to human physiological fluid. Thus, when dialysis is complete, the liquid component of a hydrogel may be substantially isosmotic with respect to human physiological fluid.

In some embodiments, a crosslinked macromolecular complex may further comprise an aqueous liquid. For example, the crosslinked macromolecular complex may absorb the aqueous liquid so that a hydrogel is formed. An aqueous liquid may comprise water with a salt dissolved in it, such as a phosphate buffer, sodium chloride, potassium chloride, etc. In some embodiments, an aqueous liquid may comprise water, sodium chloride at a concentration of about 100 mM to about 200 mM, potassium chloride at a concentration of about 2 mM to about 3 mM, and phosphate buffer at a concentration of about 5 mM to about 15 mM, wherein the pH of the liquid is about 7 to about 8.

In some embodiments, an anesthetic may be included in any composition comprising a crosslinked macromolecular complex in an amount effective to mitigate pain experienced upon injection of the composition. Examples of an anesthetic may include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclonine, ecgonidine, ecgonine, ethyl chloride, etidocaine, beta-eucaine, euprocin, fenalcomine, fomocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In some embodiments, the at least one anesthetic agent is lidocaine, such as in the form of lidocaine HCl. The concentration of lidocaine may vary. For example, some compositions may have about 0.1% to about 5%, about 0.2% to about 1.0%, or about 0.3% lidocaine by weight (w/w %) of the composition. The concentration of lidocaine in the compositions described herein can be therapeutically effective meaning the concentration may be adequate to provide a therapeutic benefit without inflicting harm to the patient.

A hydrogel may be used in a soft tissue aesthetic product. An aesthetic product includes any product that improves any aesthetic property of any part of an animal or human being. A soft tissue aesthetic product may comprise: an aesthetic device having a form suitable for injecting or implanting into human tissue; and a label comprising instructions to inject or implant the aesthetic component into human tissue; wherein the aesthetic device comprises a crosslinked macromolecular matrix described herein. Some products may comprise the crosslinked macromolecular matrix in hydrogel form.

Some embodiments include a method of improving an aesthetic quality of an anatomic feature of a human being. Improving an aesthetic quality of an anatomic feature of a human being includes improving any kind of aesthetic quality including appearance, tactile sensation, etc., and improving any anatomical feature, including those of the face, limbs, breasts, buttocks, hands, etc. Such a method may comprise injecting or implanting an aesthetic device into a tissue of the human being to thereby improve the aesthetic quality of the anatomic feature; wherein the aesthetic device comprises a crosslinked macromolecular matrix composition described herein. In some embodiments, the crosslinked macromolecular matrix used in the product may be in hydrogel form.

In some embodiments, a hydrogel of a crosslinked macromolecular complex may have a storage modulus of about 1 Pa to about 10,000 Pa, about 50 Pa to 10,000 Pa, about 50 Pa to about 6000 Pa, about 80 Pa to about 2000 Pa, about 500 Pa to about 1000 Pa, about 500 Pa to about 4000 Pa, about 500 Pa to about 5000 Pa, about 556 Pa, about 560 Pa, about 850 Pa, about 852 Pa, about 1000 Pa, or any value in a range bounded by, or between, any of these values.

In some embodiments, a hydrogel of a crosslinked macromolecular complex may have a loss modulus of about 1 Pa to about 500 Pa, about 10 Pa to 200 Pa, about 100 Pa to about 200 Pa, about 20 Pa, about 131 Pa, about 152 Pa, or any value in a range bounded by, or between, any of these values.

In some embodiments, a hydrogel of a crosslinked macromolecular complex may have an average extrusion force of about 10 N to about 50 N, about 20 N to 30 N, or about 25 N, when the hydrogel is forced through a 30 G needle syringe by moving the plunger of a 1 mL syringe containing the hydrogel at a rate of 100 mm/min for about 11 mm, and measuring the average force from about 4 mm to about 10 mm.

A crosslinked macromolecular matrix may have tunable swelling properties based on reaction conditions and hydrogel dilution. In some embodiments, a crosslinked macromolecular matrix may have a swelling ratio of about 20 to about 200. A swelling ratio is the ratio of the weight of the crosslinked macromolecular matrix after synthesis to the weight of the crosslinked macromolecular matrix without any water. The crosslinked macromolecular matrix may have a swelling power of about 1 to about 7. The swelling power is the ratio of the weight of the crosslinked macromolecular matrix when it is saturated with water to the weight of the crosslinked macromolecular matrix after synthesis.

In a crosslinking reaction, the molecular weight of a hyaluronic acid may vary. In some embodiments, a hyaluronic acid may have a molecular weight of about 200,000 daltons to about 10,000,000 daltons, about 500,000 daltons to about 10,000,000 daltons, about 1,000,000 daltons to about 5,000,000 daltons, or about 1,000,000 daltons to about 3,000,000 daltons. When the crosslinking reaction occurs, the resulting crosslinked macromolecular product may have a hyaluronic acid component derived from the hyaluronic acid in the crosslinking reaction. Thus, the ranges recited above may also apply to the molecular weight of a hyaluronic acid component, e.g. about 200,000 daltons to about 10,000,000 daltons, about 500,000 daltons to about 10,000,000 daltons, about 1,000,000 daltons to about 5,000,000 daltons, or about 1,000,000 daltons to about 3,000,000 daltons. The term "molecular weight" is applied in this situation to a portion of the matrix even though the hyaluronic acid component may not actually be a separate molecule due to the crosslinking. In some embodiments, a higher molecular weight hyaluronic acid may result in a crosslinked molecular matrix that may have a higher bulk modulus and/or less swelling.

The concentration of hyaluronic acid in an aqueous pre-reaction solution or a crosslinking reaction mixture may vary. In some embodiments, hyaluronic acid is present at about 3 mg/mL to about 100 mg/mL, about 6 mg/mL to about 24 mg/mL, about 1 mg/mL to about 30 mg/mL, about 6 mg/mL, about 9 mg/L, about 12 mg/mL, about 15 mg/L, about 16 mg/mL, about 18 mg/L, about 21 mg/L, or about 24 mg/mL. In some embodiments, higher hyaluronic acid concentration may lead to higher stiffness and/or more swelling in the crosslinked macromolecular matrix.

Any type of collagen may be used in the methods and compositions described herein. In some embodiments, collagen type I, collagen type III, collagen type IV, collagen type VI, or a combination thereof, may be used. In some embodiments, a collagen or a collagen component comprises collagen type I or collagen type III.

A collagen may be derived from cell culture, animal tissue, plant derived or recombinant means or recombinant means thereof, and may be derived from human, porcine, or bovine sources. Some embodiments comprise collagen derived from human fibroblast culture. Some embodiments comprise collagen that has been denatured to gelatin.

Collagen concentration in an aqueous pre-reaction solution or a crosslinking reaction mixture may vary. In some embodiments, collagen may be present at a concentration of about 1 mg/mL to about 40 mg/mL, about 1 mg/mL to about 15 mg/mL, about 3 mg/mL to about 12 mg/mL, about 1.7 mg/mL, about 3 mg/mL, about 6 mg/mL, about 8 mg/mL, or about 12 mg/mL.

In some embodiments, the weight ratio of hyaluronic acid to collagen in a aqueous pre-reaction solution or a aqueous pre-reaction solution or a crosslinking reaction mixture (e.g. [wt hyaluronic acid]/[wt collagen]) may be about 0.5 to about 10, about 1 to about 7, about 0.5 to about 3, about 1 to about 3, about 1 to about 2, about 1, about 2, about 3, about 3.5, about 4, about 5, 5.33, about 6, about 7, or any weight ratio in a range bounded by, and/or between, any of these values. When the crosslinking reaction occurs, the resulting crosslinked macromolecular product may have a collagen component derived from the collagen in the crosslinking reaction. Thus, the resulting crosslinked macromolecular matrix may have a weight ratio of hyaluronic acid component to collagen component that corresponds to the weight ratio in the crosslinking reaction, e.g. about 0.5 to about 10, about 1 to about 7, about 0.5 to about 3, about 1 to about 3, about 1 to about 2, about 1, about 2, about 3, about 3.5, about 4, about 5, 5.33, about 6, about 7, or any weight ratio in a range bounded by, and/or between, any of these values. A higher weight ratio of hyaluronic acid to collagen may result in a crosslinked macromolecular matrix with increased swelling, decreased stiffness, and/or decreased cell adhesion.

Certain advantageous compositions of the invention include compositions having a hyaluronic acid to collagen weight ratio of about 3:3, about 12:6, about 16:8, about 12:12, about 12:24, about 12:3, about 16:3, or about 20:3 (mg/ml).

In some embodiments, the weight ratio of hyaluronic acid to collagen in a aqueous pre-reaction solution or a aqueous pre-reaction solution or a crosslinking reaction mixture may be about 12 mg/mL of hyaluronic acid to about 6 mg/mL collagen, about 12 mg/mL of hyaluronic acid to about 12 mg/mL collagen, or about 16 mg/mL of hyaluronic acid to about 8 mg/mL collagen. In some embodiments, the collagen may be collagen type 1.

An increase in the amount of both hyaluronic acid and collagen may result in a crosslinked macromolecular matrix with increased stiffness.

A salt may help to screen the negative charges of hyaluronic acid from the positive charges of collagen, and may thus prevent precipitation of a polyionic ion complex from solution. However, high concentrations of salt may reduce the solubility of some components in solution. Thus, in some embodiments, the salt concentration of an aqueous pre-reaction solution or a crosslinking reaction mixture may be high enough to screen the charges so that the polyionic ion complex is not formed, but also low enough so that the components of the mixture remain in solution. For example, the total salt concentration of some aqueous pre-reaction solutions or crosslinking reaction mixtures may be about 10 mM to about 1 M, about 100 mM to about 300 mM, or about 150 mM. In some embodiments, a higher salt concentration may increase the efficiency of a crosslinking reaction, which may result in lower swelling and/or higher stiffness.

Some salts in an aqueous pre-reaction solution or a crosslinking reaction mixture may be non-coordinating buffers. Any non-coordinating buffer may be used that is capable of buffering the mixture and does not form coordinating complexes with coupling agents or metal atoms. Examples of suitable non-coordinating buffers may include, but are not limited to, 2-(N-morpholino)ethanesulfonic acid (MES), 3-(N-morpholino)propanesulfonic acid (MOPS), 4-(2-hydroxyethyl)-1-piperazinyl)ethanesulfonic acid (HEPES), 3-[4-(2-hydroxyethyl)-1-piperazinyl]propanesulfonic acid (HEPPS), N-cyclohexyl-2-aminoethanesulfonic acid (CHES), N-cyclohexyl-3-aminopropanesulfonic acid (CAPS), etc.

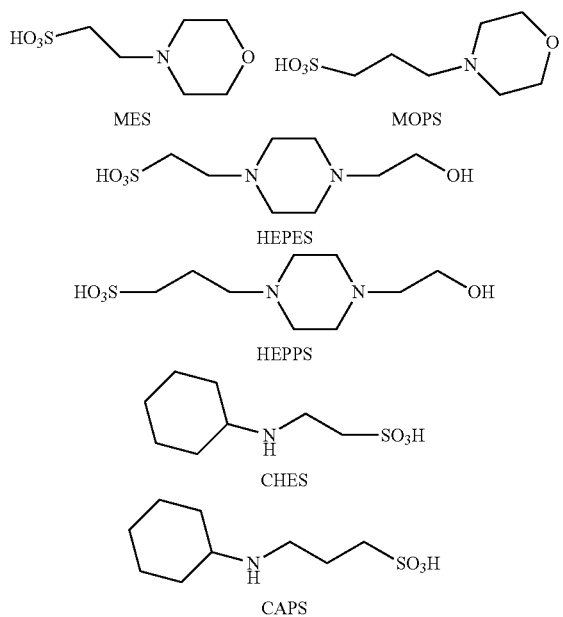

The concentration of a non-coordinating buffer may vary. For example, some aqueous pre-reaction solutions or crosslinking reaction mixtures may have a buffer concentration in a range of about 10 mM to about 1 M, about 10 mM to about 500 mM, about 20 mM to about 100 mM, or about 25 mM to about 250 mM. Some aqueous pre-reaction solutions or crosslinking reaction mixtures comprise MES at a concentration of about 20 mM to about 200 mM, about 20 mM to about 100 mM, about 100 mM, or about 180 mM.

Non-buffering salts may also be included in an aqueous pre-reaction solution or a crosslinking reaction mixture as an alternative to, or in addition, to buffering salts. Some examples may include sodium chloride, potassium chloride, lithium chloride, potassium bromide, sodium bromide, lithium bromide, and the like. The concentration of a non-buffering salt may vary. For example, some mixtures may have a non-buffering salt concentration in a range of about 10 mM to about 1 mM, about 30 mM to about 500 mM, or about 50 mM to about 300 mM. In some embodiments, sodium chloride may be present at a concentration in a range of about 0.5% w/v to about 2% about 0.9% w/v, about 1.6% w/v, about 20 mM to about 1 mM, about 40 mM to about 500 mM, about 50 to 300 mM, about 80 mM to about 330 mM, about 150 mM, or about 270 mM.

The pH of an aqueous pre-reaction solution may be lower than the pH of a crosslinking reaction mixture. If the salt content of the aqueous pre-reaction solution is low, the pH may be lower to enhance solubility of the hyaluronic acid and the collagen. If the salt content is higher, the pH may be higher in the aqueous pre-reaction solution. In some embodiments, the pH of the aqueous pre-reaction mixture is about 1 to about 8, about 3 to about 8, about 4 to about 6, about 4.7 to about 7.4, or about 5.4. For low salt concentrations, the pH may be about 1 to about 4 or about 1 to about 3. In some embodiments, a pH of around 5.4 may result in a crosslinked macromolecular matrix having higher stiffness and/or lower swelling.

In some embodiments, pH may be adjusted to neutral to allow collagen gelation or fiber formation before adding a coupling agent.

In some embodiments, the pH may be adjusted to neutral immediately prior to, around the time of, or after adding a coupling agent, such that collagen gelation is reduced or does not substantially occur.

Any water-soluble coupling agent may be used that can crosslink hyaluronic acid to collagen. Some non-limiting examples of a coupling agent include carbodiimides such as N,N'-dicyclohexylcarbodiimide (DCC), N,N'-diisopropylcarbodiimide (DIC), or 1-ethyl-3-(3-dimethylaminopropyl)carbodiimide (EDC), etc. Carbodiimide coupling agents may facilitate ester or amide bond formation without becoming part of the linkage. In other words, an ester bond or an amide bond may comprise atoms from a carboxylate group from one of hyaluronic acid or collagen, and a hydroxyl group or an amine group from the other. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM.

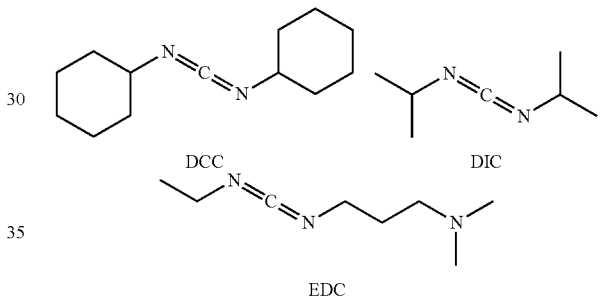

A crosslinking reaction includes any reaction wherein hyaluronic acid is covalently linked to collagen in a plurality of (e.g. more than 1) positions. In some embodiments, a crosslinking reaction may be represented by Scheme 1 below. In Scheme 1, only some of the reacting functional groups are depicted. Additionally, some functional groups that may potentially react in a crosslinking reaction, but may remain unreacted. Unreacted functional groups such as these are not shown. For example, OH, $CO_2H$, —NHCOCH$_3$, and other groups on hyaluronic acid that are not shown may react, but may also remain unreacted. Similarly, collagen may have additional groups that may react, but may also remain unreacted, such as OH, SH, $CO_2H$, $NH_2$, etc. Additionally, fewer groups may react than those depicted.

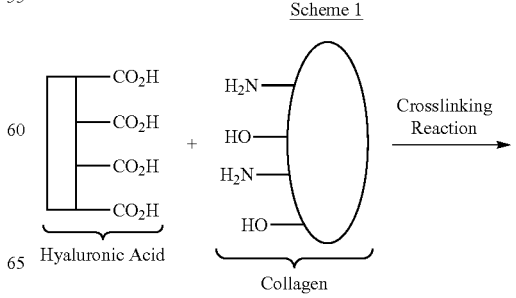

-continued

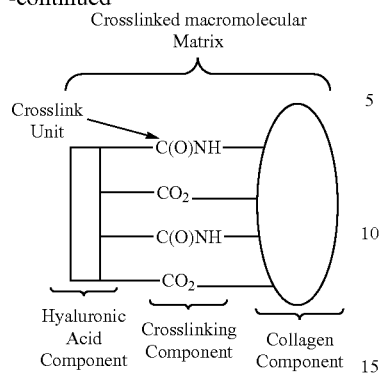

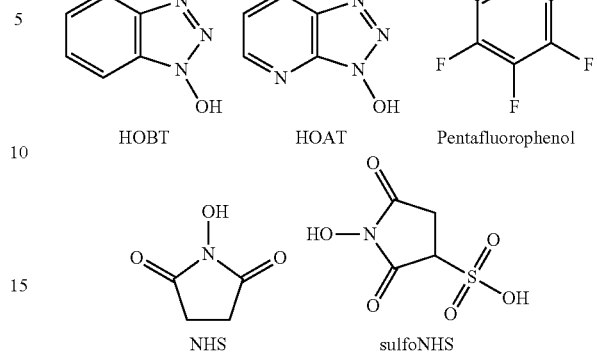

In Scheme 1, functional groups such as CO₂H on hyaluronic acid may react with functional groups on collagen such as NH₂ and OH to form several crosslink units. The crosslink units together make up the crosslinking component. In Scheme 1, a coupling component does not become part of a crosslink unit. However, for some coupling agents, at least part of a coupling agent may be incorporated into a crosslink unit. The hyaluronic acid component includes hyaluronic acid that has reacted to become part of a crosslinked macromolecular matrix. The collagen component includes collagen that has reacted to become part of a crosslinked macromolecular matrix. In addition to the crosslinking between hyaluronic acid and collagen, hyaluronic acid or collagen may be partially self-crosslinked. Thus, Scheme 1 is presented for convenience in understanding the crosslinking reaction, but does not necessarily reflect an actual chemical structure. For example, a crosslinked molecular matrix may be a network of hyaluronic acid macromolecules and collagen macromolecules, with many macromolecules crosslinked to more than one macromolecule.

As a result of a crosslinking reaction, a crosslinked macromolecular matrix may comprise a crosslinking component that crosslinks or covalently connects the hyaluronic acid component to the collagen component. As explained above, a crosslink component comprises a plurality of crosslink units, or individual covalent bonding links, between the hyaluronic acid component and the collagen component. A crosslink unit may simply be a direct bond between a hyaluronic acid component and a collagen component, so that the coupling agent may not be incorporated into the crosslinked macromolecular matrix. Alternatively, a crosslink unit may contain additional atoms or groups from the coupling agent such that at least a portion of the coupling agent may become part of the crosslinked macromolecular matrix. At least a portion of the crosslink units comprise an ester bond or an amide bond. In some embodiments, at least a portion of the crosslink units may be —CON— or —CO₂—, where the N is a nitrogen from an amino acid residue.

An activating agent may be used to increase the rate of the crosslinking reaction and the number of crosslink units in the final product. In some embodiments, an activating agent may be a triazole such as hydroxybenzotriazole (HOBT) or 1-hydroxy-7-azabenzotriazole (HOAT); a fluorinated phenol such as pentafluorophenol; a succinimide such as N-hydroxysuccinimide (NHS) or N-hydroxysulfosuccinimide (sulfoNHS), and the like.

The concentration of an activating agent may vary. In some embodiments, the activating agent may have a concentration of about 2 mM to about 200 mM, about 2 mM to about 50 mM, about 20 mM to about 100 mM, or about 50 mM. In some embodiments, the activating agent may be NHS or sulfoNHS is at a concentration of about 2 mM to about 50 mM. In some embodiments, the activating agent may be N-hydroxysulfosuccinimide, sodium salt, at a concentration of about 20 mM to about 100 mM, or about 50 Mm.

In some embodiments, a crosslinking reaction mixture may comprise a carbodiimide coupling agent and an activating agent. In some embodiments, the coupling agent is EDC and the activating agent is NHS or sulfoNHS. In some embodiments EDC is present at a concentration of about 2 mM to about 50 mM and NHS or sulfoNHS is present at about 2 mM to about 50 mM.

In some embodiments, a crosslinking reaction mixture may comprise hyaluronic acid at a concentration of about 3 mg/mL, human collagen type III at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 6 mg/mL, human collagen type III at a concentration of about 6 mg/mL, 2-(N-morpholino)ethanesulfonic acid at a concentration of about 180 mM, sodium chloride at a concentration of about 1.60.9 wt % or about 270 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL of, rat collagen type I at a concentration of about 8 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, rat collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, rat tail collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.3.

In some embodiments, a crosslinking reaction mixture may comprise hyaluronic acid at a concentration of about 3 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL, human collagen type I at a concentration of about 8 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, human collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 24 mg/mL, human collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 9 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 15 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 18 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 21 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 9 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 15 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 18 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 21 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 1 mg/mL to about 20 mg/mL, porcine collagen type I at a concentration of about 1 mg/mL to about 15 mg/mL, 2-(N-morpholino)ethanesulfonic acid at a concentration of about 20 mM to about 200 mM, sodium chloride at a concentration of about 0.5 wt % to about 2 wt % or about 80 mM to about 330 mM, 1-ethyl-3-(3-dimethylaminopropyl)carbodiimide at a concentration of about 20 mM to about 100 mM, and N-hydroxysulfosuccinimide sodium salt at a concentration of about 20 mM to about 100 mM, wherein the solution has a pH of about 4 to about 6.

Aspects of the present specification provide, in part, a composition comprising a hydrogel as described herein, and a cellular component. In an embodiment, a cellular component comprises cells obtained from adipose tissue. In some embodiments, a cellular component comprises adipocytes, adipose-derived stem cells, stromal vascular fraction cells, or a combination thereof.

As used herein, the terms "adipose tissue," "fat," "fat tissue", or "fatty tissue" include loose fibrous connective tissue comprising fat cells (adipocytes) and multiple types of regenerative cells, and may comprise brown and/or white adipose tissue taken from any body site, such as, e.g., subcutaneous, omental/visceral, interscapular, or mediastinal. It may be obtained from any organism having adipose tissue, or the adipose tissue used may be from a primary cell culture or an immortalized cell line.

Adipose tissue may be collected from the same individual who is undergoing the soft tissue replacement procedure (autograft), from a donor individual who is not the same individual as the one undergoing the soft tissue replacement procedure (allograft), or from an animal source (xenograft). As used herein, the term "autotransplantation" refers to the transplantation of organs, tissues, or cells from one part of the body to another part in the same individual, i.e., the donor and recipient are the same individual. Tissue transplanted by such "autologous" procedures is referred to as an autograft or autotransplant. As used herein, the term "allotransplantation" refers to the transplantation of organs, tissues, or cells from a donor to a recipient, where the donor and recipient are different individuals, but of the same species. Tissue transplanted by such "allologous" procedures is referred to as an allograft or allotransplant. As used herein, the term "xenotransplantation" refers to the transplantation of organs, tissues, or cells from a donor to a recipient, where the donor is of a different species as the recipient. Tissue transplanted by such "xenologous" procedures is referred to as a xenograft or xenotransplant.

Adipose tissue can be collected by any procedure that can harvest adipose tissue useful for the compositions and methods disclosed herein, including, without limitation a liposuction (lipoplasty) procedure or a lipectomy procedure. Procedures useful for collecting adipose tissue should minimize the trauma and manipulation associated with adipose tissue removed. Adipose tissue may be harvested from any suitable region, including, without limitation, a mammary region, an abdominal region, a thigh region, a flank region, a gluteal region, a trochanter region, or a gonadal region. Procedures useful for collecting adipose tissue are well known to a person of ordinary skill in the art. The selected procedures may be performed concomitantly with liposculpture.

A liposuction procedure harvests adipose tissue by aspirating the tissue using a cannula. The cannula may be connected to a syringe for manual aspiration or to a power assisted suction device, like an aspirator, adapted to collect the adipose tissue into a vacuum bottle. A liposuction procedure does not maintain an intact blood supply of the harvested tissue. The syringe may be a 10, 20 or 60 mL syringe fitted with a 12 or 14 gauge cannula. Non-limiting examples of liposuction procedures include suction-assisted liposuction (SAL), ultrasound-assisted liposuction (UAL), power-assisted liposuction (PAL), twin-cannula (assisted) liposuction (TCAL or TCL), or external ultrasound-assisted liposuction (XUAL or EUAL), or water-assisted liposuction (WAL). In addition, the liposuction procedures listed above can be used with any of the following procedures that vary the amount of fluid injected during the procedure, such as, e.g., dry liposuction, wet liposuction, super-wet liposuction, tumescent liposuction, or laser-assisted liposuction. An autologous soft tissue transfer procedure typically uses adipose tissue collected from a liposuction procedure.

Although the harvested tissue may be used directly to make the disclosed compositions, it is more typically processed to purify and/or enrich for healthy adipocytes and regenerative cells. For example, the harvested adipose tissue may be separated from any debris and/or contaminants such as, e.g., blood, serum, proteases, lipases, lipids and other oils, and/or other bodily fluids; tumescent fluid and/or other materials used in the liposuction procedure; and/or other impurities suctioned during the procedure. Methods useful in separating debris and/or contaminants from adipose tissue useful to make the disclosed compositions, including, without limitation, centrifugation, sedimentation, filtration, and/or absorption. In addition, or alternatively, the harvested adipose tissue may be processed by washing is a physiological buffer like saline to remove any debris and/or contaminants.

A lipectomy procedure harvests adipose tissue by surgical excision from a donor site in a manner that minimizes damage to the blood supply of the tissue using standard surgical operative procedures. This harvested tissue is then implanted into the region needing the soft tissue replacement. A tissue flap or tissue graft procedure typically uses adipose tissue collected from a lipectomy procedure. A tissue flap is a section of living tissue that maintained its blood supply as the tissue is moved from one area of the body to another.

A local flap uses a piece of skin and underlying tissue that lie adjacent to the wound, including adipose tissue. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. As an example, the transverse rectus abdominis myocutaneous) flap (TRAM flap) is a tissue flap procedure that uses muscle, fat and skin from an abdomen to create a new breast mound after a mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is a patch of healthy skin that is taken from one area of the body, called the "donor site," and used to cover another area where skin is missing or damaged. There are three basic types of skin grafts. A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are desired. As its name implies, a full-thickness (all layers) section of skin from the donor site are lifted. A composite graft is used when the wound to be covered needs more underlying support, as with skin cancer on the nose. A composite graft requires lifting all the layers of skin, adipose tissue, and sometimes the underlying cartilage from the donor site.

The amount of adipose tissue collected will typically vary from individual to individual and can depend on a number of factors including, but not limited to, amount of adipose tissue required for the soft tissue replacement method, aesthetic expectations, age, body habitus, coagulation profile, hemodynamic stability, co-morbidities, and physician preference. A liposuction procedure may harvest from about 1 mL to about 1500 mL of adipose tissue. A lipectomy procedure typically harvests about 1 g to about 5,000 g.

Adipose tissue comprises multiple types of regenerative cells. As used herein, the term "regenerative cell" refers to any cells that cause or contribute to complete or partial regeneration, restoration, or substitution of structure or function of an organ, tissue, or physiologic unit or system to thereby provide a therapeutic, structural or cosmetic benefit. Examples of regenerative cells include stem cells, progenitor cells, and precursor cells.

As used herein, the term "stem cell" refers to a multipotent regenerative cell with the potential to differentiate into a variety of other cell types that perform one or more specific functions and has the ability to self-renew. Some of the stem cells disclosed herein may be pluripotent. Exemplary examples of stem cells include, without limitation, adipose-derived stem cells (ASCs; adipose-derived stromal cells), endothelial-derived stem cells (ESCs), hemopoietic stem cells (HSCs), and mesenchymal stem cells (MSCs). Examples of differentiation include angiogenesis, neovascularization, adipogenesis and collagenesis.

As used herein, the term "progenitor cell" refers to an oligopotent regenerative cell with the potential to differentiate into more than one cell type, or a unipotent regenerative cell with the potential to differentiate into only a single cell type, that perform(s) one or more specific functions and has limited or no ability to self-renew. Exemplary examples of progenitor cells include, without limitation, endothelial progenitor cells, keratinocytes, monoblasts, myoblasts, and pericytes.

As used herein, the term "precursor cell" refers to a unipotent regenerative cell with the potential to differentiate into one cell type that performs one or more specific functions and may retain extensive proliferative capacity that enables the cells to proliferate under appropriate conditions. Exemplary examples of precursor cells include, without limitation, adipoblast (lipoblast or preadipocytes), de-differentiated adipocytes, angioblasts, endothelial precursor cells, fibroblasts, lymphoblasts, and macrophages.

A hydrogel composition disclosed herein may enhance differentiation of the multiple regenerative cells from the adipose tissue. In one embodiment, a hydrogel composition disclosed herein enhances differentiation of the multiple regenerative cells from the adipose tissue as compared to adipose tissue alone. In aspects of this embodiment, a hydrogel composition disclosed herein enhances differentiation of the multiple regenerative cells from the adipose tissue by at least about 50% at least about 100%, at least about 150%, at least about 200%, at least 250%, at least about 300%, at least about 350%, at least about 400%, at least about 450%, at least about 500%, at least about 750%, or at least about 1000% as compared to adipose tissue alone. In aspects of this embodiment, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue alone.

In another embodiment, a hydrogel composition disclosed herein enhances differentiation of the multiple regenerative cells from the adipose tissue as compared to adipose tissue with a hydrogel composition that is substantially identical except that the hyaluronic acid component and the collagen component are not crosslinked. In aspects of this embodiment, a hydrogel composition disclosed herein enhances differentiation of the multiple regenerative cells from the adipose tissue by at least about 50% at least about 100%, at least about 150%, at least about 200%, at least 250%, at least about 300%, at least about 350%, at least about 400%, at least about 450%, at least about 500%, at least about 750%, or at least about 1000% as compared to adipose tissue with a hydrogel composition that is substantially identical except that the hyaluronic acid component and the collagen component are not crosslinked. In aspects of this embodiment, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue with a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In yet another embodiment, a hydrogel composition disclosed herein enhances differentiation of the multiple regenerative cells from the adipose tissue as compared to adipose tissue with a hydrogel composition that is substantially identical except that the collagen component is absent. In aspects of this embodiment, a hydrogel composition disclosed herein enhances differentiation of the multiple regenerative cells from the adipose tissue by at least about 50% at least about 100%, at least about 150%, at least about 200%, at least 250%, at least about 300%, at least about 350%, at least about 400%, at least about 450%, at least about 500%, at least about 750%, or at least about 1000% as compared to adipose tissue with a hydrogel composition that is substantially identical except that the collagen component is absent. In aspects of this embodiment, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue with a hydrogel composition that is substantially identical except that the collagen component is absent. In another aspect of this embodiment, a hydrogel composition that is substantially identical to a hydrogel composition disclosed herein except that the collagen component is absent comprises hyaluronic acid at a concentration of about 16 mg/mL or about 24 mg/mL and water.

Harvested adipose tissue useful in compositions of the invention can be supplemented with regenerative cells such as, e.g., stem cells, progenitor cells, and precursor cells. Regenerative cells may promote new blood vessel formation, diminish necrosis, and/or promote a supportive microenvironment in the transplanted tissue, thereby improving survivability of the transplanted tissue. Regenerative cells can be obtained from a variety of sources. For example, adipose tissue is rich in regenerative cells that have the ability to restore and reconstruct various soft tissue defects in response to local differentiation clues from the recipient site. As such, a portion of the collected adipose tissue may be further processed in order to purify regenerative cells that can then be added back to the remainder of the harvested adipose tissue in order to enrich this material for these cells. Exemplary methods describing such cell enrichment procedures can be found in, e.g., Hedrick and Fraser, Methods of Using Adipose Tissue-Derived Cells in Augmenting Autologous Fat Transfer, U.S. Patent Publication 2005/0025755, Yoshimura, et al., Characterization of Freshly Isolated and Cultured Cells Derived form the Fatty and Fluid Portions of liposuction Aspirates, J. Cell. Physiol. 208: 1011-1041 (2006); Yoshimura, et al., Cell-Assisted Lipotransfer for Facial Lipoatrophy: Effects of Clinical Use of Adipose-Derived Stem Cells, Dermatol. Surg. 34: 1178-1185 (2008); Yoshimura, et al., Cell-Assisted Lipotransfer for Cosmetic Breast Augmentation: Supportive Use of Adipose-Derived Stem/Stromal Cells, Aesth. Plast. Surg. 32: 48-55 (2008); each of which is hereby incorporated by reference in its entirety.

In addition, harvested adipose tissue can be supplemented with regenerative cells obtained from cell cultures, such as, e.g., primary cell cultures and established cell cultures. For example, a portion of harvested adipose tissue from an individual can be cultured in a manner to produce primary cell cultures enriched for regenerative cells. Alternatively, established cell lines derived from regenerative cells from adipose tissue, or another tissue source, can be cultured, harvested, and added to adipose tissue collected form an individual. Exemplary methods describing such cell culture compositions and procedures can be found in, e.g., Casteilla, et al., Method for Culturing Cells Derived from the Adipose Tissue and Uses Thereof, U.S. Patent Publication 2009/0246182; Chazenbalk, et al, Methods of Producing Preadipocytes and Increasing the Proliferation of Adult Adipose Stem/Progenitor Cells, U.S. Patent Publication 2009/0317367; Kleinsek and Soto, Augmentation and Repair of Sphincter Defects with Cells Including Adipocytic Cells, U.S. Patent Publication 2008/0299213; Rehman, et al., Secretion of Angiogenic and Antiapoptotic Factors by Human Adipose Stromal Cells, Circulation 109: r52-r58 (2004); Kilroy, et al., Cytokine Profile of Human Adipose-Derived Stem Cells: Expression of Angiogenic, Hematopoietic, and Pro-Inflammatory Factors, J. Cell. Physiol. 212: 702-709 (2007); each of which is hereby incorporated by reference in its entirety.

Harvested adipose tissue may be immediately used to make the compositions disclosed herein. Alternatively, harvested adipose tissue, whether unprocessed or processed, may be stored for used at some future date. Harvested tissue is typically stored using a slow freezing method of the tissue to −20° C., with or without cryopreservatives. Stored adipose tissue can typically be stored for at least 6 months.

In some embodiments, a hydrogel composition as described herein may include a hyaluronic acid:collagen weight ratio of 3 to 1. The concentrations of hyaluronic acid can be from about 12 mg/mL to about 24 mg/mL and the collagen can be from about 3 mg/mL to about 12 mg/mL. The collagen may be collagen type 1. Further, the hydrogel composition may be used for fat grafting applications as an additive. The source of the collagen can vary, but can be human recombinant (cell derived or plant derived), porcine, bovine or ovine. The hydrogels can be formed with an EDC crosslinker and NHS as an activating agent.

Hydrogel compositions described herein can further have a storage modulus (G') and a loss modulus (G") each independently between about 500 Pa and about 4,000 Pa.

A general method of making hydrogel compositions as described herein can be achieved as follows. First, lyophilized hyaluronic acid fibers can be added to a concentrated (e.g. hydrated) collagen solution. The pH can then be managed by the addition of one or more buffer salt and/or the addition of a base (e.g. NaOH). After the pH has been managed, the mixture can be hydrated and thoroughly mixed followed by addition of crosslinking agents. The crosslinking agents can be solids (e.g. powder). The hyaluronic acid and collagen can be left to react. Once reacted, the resultant gel can be particle sized through a filter mesh (e.g. 100 μm) and can be dialyzed with buffer to purify (e.g. against any unused or unreacted crosslinker). The gel can then be sterilized (e.g. using isopropanol). This sterilization can also occur prior to purification. Once sterilized the gel may be ready for administration. The sterilized gel can also be further mixed within adipose tissue (e.g. human).

The sterilized gel either mixed with adipose tissue or not mixed with adipose tissue can be administered as described herein to treat a condition of, for example, the face, breast, hands, etc.

Example 1

Hyaluronic acid, 2 MDa molecular weight, (HTL Biotech) was dissolved in human collagen(I) solution in 0.01 N hydrochloric acid (Advanced BioMatrix). Sodium chloride was added at 0.9 wt % and 2-(morpholino)ethanesulfonic acid was added at 100 mM to the solution and mixed. The hyaluronic acid was allowed to hydrate for 1 hr and the solution was homogenized by syringe-to-syringe mixing. The pH of the solution was adjusted to 5.4 by addition of 1 N sodium hydroxide. 1-Ethyl-3-(3-dimethylaminopropyl) carbodiimide (50 mM) and N-hydroxysulfosuccinimide sodium salt (50 mM) were added to the hyaluronic acid/collagen solution and quickly mixed by syringe-to-syringe transfer. The solution was transferred to a glass vial and centrifuged for 5 min at 4000 RPM to remove air bubbles. The resulting gel was allowed to react for 16 hrs at 4° C. The gel was then particulated through a 100 micron pore-sized mesh. Following sizing, the gel was sterilized by dialysis through a 20 kDa molecular-weight cut-off cellulose ester membrane against 70% isopropanol/30% water for 3 hrs at 4° C. Dialysis was then continued against sterile phosphate buffer, pH 7.4, for 48 hrs at 4° C. with four changes of buffer. The gel was then dispensed into syringes under aseptic conditions.

This procedure was used to produce hydrogels with varying concentrations of hyaluronic acid and collagen. When required, human collagen(I) in 0.01 N hydrochloric acid was concentrated from 3 mg/mL to the desired reaction concentration in 20 kDa molecular-weight cut-off centrifugal filtration devices. A 50 mL sample of each gel was synthesized, sterilized by exposure to 70% isopropanol, and purified by dialysis against phosphate buffer, pH 7.4. The gels synthesized are described in Table 1.

TABLE 1

Hyaluronic acid-human collagen(I) hydrogel synthesis concentrations

| Sample ID | [HA] (mg/mL) | [Col(I)] (mg/mL) |
|---|---|---|
| A | 3 | 3 |
| B | 12 | 6 |
| C | 16 | 8 |
| D | 12 | 12 |
| E | 24 | 12 |

Example 2

Oscillatory parallel plate rheology was used to characterize the mechanical properties of the hydrogels synthesized in Example 1 using an Anton Paar MCR 301. A plate diameter of 25 mm was used at a gap height of 1 mm. A frequency sweep from 0.1 to 10 Hz at a fixed strain of 2% with logarithmic increase in frequency was applied followed by a strain sweep between 0.1% and 300% at a fixed frequency of 5 Hz with logarithmic increase in strain. The storage modulus (G') and loss modulus (G") were recorded from frequency sweep measurements at 5 Hz. Values from measurements of samples from Example 1 are presented in Table 2.

TABLE 2

Rheological properties of hyaluronic acid-collagen(I) hydrogels

| Sample ID | [HA] mg/mL) | [Col(I)] (mg/mL) | G' (Pa) | G"(Pa) |
|---|---|---|---|---|
| A | 3 | 3 | 199 | 24.6 |
| B | 12 | 6 | 1260 | 154 |
| C | 16 | 8 | 2450 | 288 |
| D | 12 | 12 | 3160 | 420 |
| E | 24 | 12 | 5440 | 433 |
| F | 12 | 3 | 1100 | 52.2 |
| G | 16 | 3 | 1490 | 60.6 |
| H | 20 | 3 | 1770 | 49.5 |

Example 3

Swelling ratios were determined relative to initial water content for each of the samples in Example 1 by increase in weight when equilibrated with phosphate buffer. For each gel, approximately 1 mL was injected into a 15 mL Falcon tube and weighed followed by addition of 10 mL of phosphate buffered saline, pH 7.4. The gels were thoroughly mixed with the buffer and vortexed for 30 seconds. The gels were then allowed to equilibrate in the buffer for 48 hrs at 4° C. After this time, the suspensions were centrifuged at 4000 RPM in a swinging bucket rotor for 5 minutes. The supernatant buffer was then decanted and the weight of the swollen gel was measured. The swelling ratio was determined by dividing the final weight of the swollen gel by the weight of the initial gel. The swelling results of samples from Example 1 are presented in Table 3. A swelling ratio less than 1 indicates that the gel lost water upon equilibration and centrifugation.

TABLE 3

Swelling ratios of hyaluronic acid-collagen(I) hydrogels

| Sample ID | [HA] (mg/mL) | [Col(I)] (mg/mL) | Swelling ratio |
|---|---|---|---|
| A | 3 | 3 | 0.96 |
| B | 12 | 6 | 1.67 |
| C | 16 | 8 | 1.69 |
| D | 12 | 12 | 1.49 |
| E | 24 | 12 | 1.65 |

Example 4

Samples of gels from Example 1 were tested for their ability to support human adipose derived stem cell (ASC) viability. In 96-well plates, 50 μL gel beds were created in triplicate from gels of Example 1. Culture-expanded ASCs (Invitrogen) were plated at 5,000 cells/cm$^2$ on the gel beds in MesenPro RS medium with growth supplement (Invitrogen, CA). The cells were cultured for 18 hrs at 37° C., 5% $CO_2$, after which the MTT assay (ATCC, VA) was performed. The tetrazolium compound MTT (3-[4, 5-dimethylthiazol-2-yl]-2, 5-diphenyltetrazolium bromide) is added to the wells and the cells are incubated. MTT is reduced by metabolically active cells to insoluble purple formazan dye crystals. Detergent is then added to the wells, solubilizing the crystals so the absorbance can be read using a spectrophotometer at 570 nm, Cells adhered to the gels and exhibited a spread morphology. The viability of hASCs increased with increasing total biopolymer and collagen concentrations. Viability relative to tissue culture polystyrene (TCP) are shown in Table 4.

TABLE 4

ASC viability on hyaluronic acid-collagen(I) hydrogels

| Sample | [HA] (mg/mL) | [Col(I)] (mg/mL) | Viability (relative to TCP) |
|---|---|---|---|
| A | 3 | 3 | 94% |
| B | 12 | 6 | 120% |
| C | 16 | 8 | 140% |
| D | 12 | 12 | 245% |
| E | 24 | 12 | 350% |

Example 5

Samples of HA-Col(I) from Example 1 were tested for their ability to support ASC proliferation. In 96-well plates, 50 µL gel beds were created in triplicate from the hyaluronic acid-collagen(I) hydrogels. ASCs (Invitrogen) were plated at 5,000 cells/cm$^2$ on the gel beds in MesenPro RS medium with growth supplement (Invitrogen). ASCs were cultured for one week at 37° C., 5% $CO_2$, and proliferation was determined by MTT assay at 3, 5, and 7 days with media changes every 2 days. Tissue culture polystyrene (TCP) was used as positive control, while crosslinked HA, not containing collagen, was used as an additional control to establish the effect of collagen in HA-Col(I) formulations. Proliferation rates at day 3, relative to HA and TCP, were determined. Incorporation of collagen I (at concentration ≥6 mg/mL) dramatically improved HA gel's support for hASC proliferation, reaching proliferation rates comparable to TCP positive control (Table 5).

TABLE 5 hASC proliferation (3-day) on hyaluronic acid-collagen(I) hydrogels

| Example | [HA] (mg/mL) | [Col(I)] (mg/mL) | Proliferation (%) (relative to HA) | Proliferation (%) (relative to TCP) |
|---|---|---|---|---|
| A | 3 | 3 | 371 ± 63 | 95 ± 143 |
| B | 12 | 6 | 354 ± 60 | 91 ± 15 |
| C | 16 | 8 | 460 ± 60 | 123 ± 45 |
| D | 12 | 12 | 381 ± 119 | 95 ± 7 |
| E | 24 | 12 | 415 ± 91 | 106 ± 12 |

Example 6

Samples of hyaluronic acid-collagen(I) matrices from Example 1 were assessed for their ability to allow diffusion of pro-angiogenic (vascular endothelial growth factor, VEGF) and adipose tissue-specific growth factors (adiponectin, leptin). Improved diffusion to any or all of these growth factors would support the enhanced survival of co-grafted tissue, especially fat, since nutrient diffusion may be important for sustained tissue viability. To do this, 100 µL of each hydrogel tested was loaded into a 8 µm transwell (24 well plate) in order to make a gel column. Known concentrations of target factors were loaded on top of the gel, diluted in fibroblast basal medium (Cat#PCS-201-030, ATCC). Plates were allowed to incubate at 37° C. with 5% $CO_2$ in a tissue culture incubator, for 60 hours, thereby allowing the factors to diffuse through the gels. Diffusion of the specified factors through each hydrogel was measured by ELISA in the supernatant in the bottom chamber of the wells. Results indicated improved diffusion of the targeted factors compared to the reference, crosslinked HA hydrogel not containing collagen (Table 6).

TABLE 6

Hyaluronic acid-human collagen (I) hydrogels showed improved diffusion of adipokines

| Sample | Adiponectin (%) | Leptin (%) | VEGF (%) |
|---|---|---|---|
| A | 250 ± 25 | 263 ± 1 | 225 ± 28 |
| B | 84 ± 9 | 171 ± 11 | 147 ± 6 |
| C | 85 ± 4 | 196 ± 43 | 155 ± 33 |
| D | 92 ± 9 | 152 ± 4 | 127 ± 5 |
| E | 130 ± 79 | 155 ± 19 | 111 ± 15 |

Note:
diffusion compared to the reference HA gel, lacking collagen type 1.

Example 7

The hyaluronic acid-collagen(I) gels from Example 1 were mixed with human lipoaspirate at 2:1 lipo:gel ratio in a nude mouse model to assess the gels' ability to enhance fat graft viability and volume retention. Human lipoaspirate tissue was procured through means of ultrasound- or suction-assisted liposuction under informed consent, then consecutively centrifuged and washed 3× at 30 g for 5 min, in 1× phosphate buffered saline without cations (PBS, Invitrogen) inside a sterile biosafety cabinet. Next, 10 mL of washed lipoaspirate was transferred to a clean 100 mL sterile reservoir. To this tissue, 5 mL of sterile hydrogel was added and carefully blended by hand using a sterile spatula. The mixing procedure required 5 to 10 minutes of constant stirring with mechanical disruption of large pieces of tissue to generate a homogenous mixture. Then 1 mL syringes were filled with lipoaspirate/hydrogel until the plunger reached the 1 mL mark. The syringe was then capped with a sterile female luer-lock cap and maintained on ice blocks until use. Lipoaspirate/hydrogel mixes were implanted as 1 mL bolus subcutaneously on the dorsum of female 6-week-old nude mice under anesthesia with two injections per mouse. Each gel/lipo mixture was implanted through a small incision by 16 G cannula and the incision closed using surgical glue. A total of 14 injections of each material were made. Syringes were weighed before and after injection to determine the weight of injected material. After 6 weeks, the gels were harvested and weight and volume (using liquid displacement) were determined for each sample. Samples were also processed for histology by H&E staining.

Example 8

Hyaluronic Acid-Human Collagen(I) Hydrogel Compositions for Fat Grafting

Hyaluronic acid, 2 MDa molecular weight, (HTL Biotech) was dissolved in human collagen(I) solution in 0.01 N hydrochloric acid (Advanced BioMatrix). Sodium chloride was added at 0.9 wt % and 2-(morpholino)ethanesulfonic acid was added at 100 mM to the solution and mixed. The hyaluronic acid was allowed to hydrate for 1 hr and the solution was homogenized by syringe-to-syringe mixing. The pH of the solution was adjusted to 5.4 by addition of 1 N sodium hydroxide. 1-Ethyl-3-(3-dimethylaminopropyl) carbodiimide (50 mM) and N-hydroxysulfosuccinimide sodium salt (50 mM) were added to the hyaluronic acid/collagen solution and quickly mixed by syringe-to-syringe transfer. The solution was transferred to a glass vial and centrifuged for 5 min at 4000 RPM to remove air bubbles. The resulting gel was allowed to react for 16 hrs at 4° C. The gel was then particulated through a 100 micron pore-sized mesh. Following sizing, the gel was sterilized by dialysis through a 20 kDa molecular-weight cut-off cellulose ester membrane against 70% isopropanol/30% water for 3 hrs at 4° C. Dialysis was then continued against sterile phosphate buffer, pH 7.4, for 48 hrs at 4° C. with four changes of buffer. The gel was then dispensed into syringes under aseptic conditions.

This procedure was used to produce hydrogels with varying concentrations of hyaluronic acid and collagen. When required, human collagen(I) in 0.01 N hydrochloric acid was concentrated from 3 mg/mL to the desired reaction concentration in 20 kDa molecular-weight cut-off centrifugal filtration devices. A 50 mL sample of each gel was synthesized, sterilized by exposure to 70% isopropanol, and purified by dialysis against phosphate buffer, pH 7.4. The gels synthesized are described in Table 7.

TABLE 7

Hyaluronic acid-human collagen(I) hydrogel synthesis concentrations

| Sample ID | [HA] (mg/mL) | [Col(I)] (mg/mL) |
|---|---|---|
| A | 3 | 3 |
| B | 12 | 6 |
| C | 16 | 8 |
| D | 12 | 12 |
| E | 16 | 3 |
| F | 24 | 12 |
| G | 21 | 6 |

Example 9

Figure 1B:
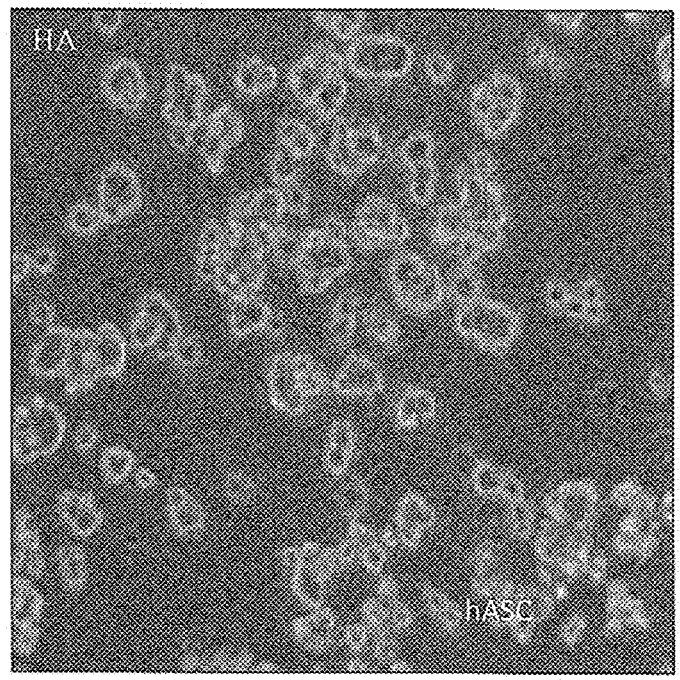

Hyaluronic Acid-Human Collagen(I) Hydrogels Stimulate Human Adipose Derived Stem Cell (hASC) Attachment and Proliferation Samples of HA-Col(I) were tested for their ability to support hASC attachment and proliferation. To evaluate cell attachment, hASCs were cultured on hydrogels in serum free, basal medium for 18 hrs. A sign of cell attachment is demonstrated in the cell's ability to extend processes through the gel. Bright field microscopy demonstrated at 18 hrs that hASCs attached and spread on HA-Col(I) hydrogels, but not on HA gels without human collagen(I) (FIGS. 1A and 1B). Actin-phalloidin staining, to observe individual actin filaments in fixed cultures, further confirmed this result showing clear spreading of cells in HA-Col(I) gels only (data not shown).

To evaluate cell proliferation, in 96-well plates, 50 µL gel beds were created in triplicate from the hyaluronic acid-collagen(I) hydrogels. hASCs (Invitrogen) were plated at 5,000 cells/cm² on the gel beds in MesenPro RS medium with growth supplement (Invitrogen). ASCs were cultured for one week at 37° C., 5% $CO_2$, and proliferation was determined by MTT assay at 3, 5, and 7 days with media changes every 2 days. Tissue culture polystyrene (TCP) was used as positive control, while crosslinked hyaluronic acid (HA) not containing collagen, was used as an additional control to establish the effect of collagen in HA-Col(I) formulations. Proliferation rates at day 5, relative to HA(−) gels not containing collagen, were determined. Incorporation of collagen I significantly improved HA gel's support for hASC proliferation (Table 8).

TABLE 8 hASC proliferation (5-day) on hyaluronic acid-collagen(I) hydrogels

| Sample | HA (mg/mL) | Col1 (mg/mL) | Percent to HA(—) (%) |
|---|---|---|---|
| HA(—) [control] | 16 | 0 | 100 ± 5 |
| HA-CN (9.3) | 9 | 3 | 337 ± 24 |
| HA-CN (12.3) | 12 | 3 | 254 ± 28 |
| HA-CN (15.3) | 15 | 3 | 307 ± 22 |
| HA-CN (18.3) | 18 | 3 | 289 ± 26 |
| HA-CN (21.3) | 21 | 3 | 231 ± 46 |
| HA-CN (9.6) | 9 | 6 | 341 ± 28 |
| HA-CN (12.6) | 12 | 6 | 501 ± 53 |
| HA-CN (15.6) | 15 | 6 | 317 ± 34 |
| HA-CN (18.6) | 18 | 6 | 306 ± 39 |
| HA-CN (21.6) | 21 | 6 | 300 ± 52 |

Example 10

Figure 2:
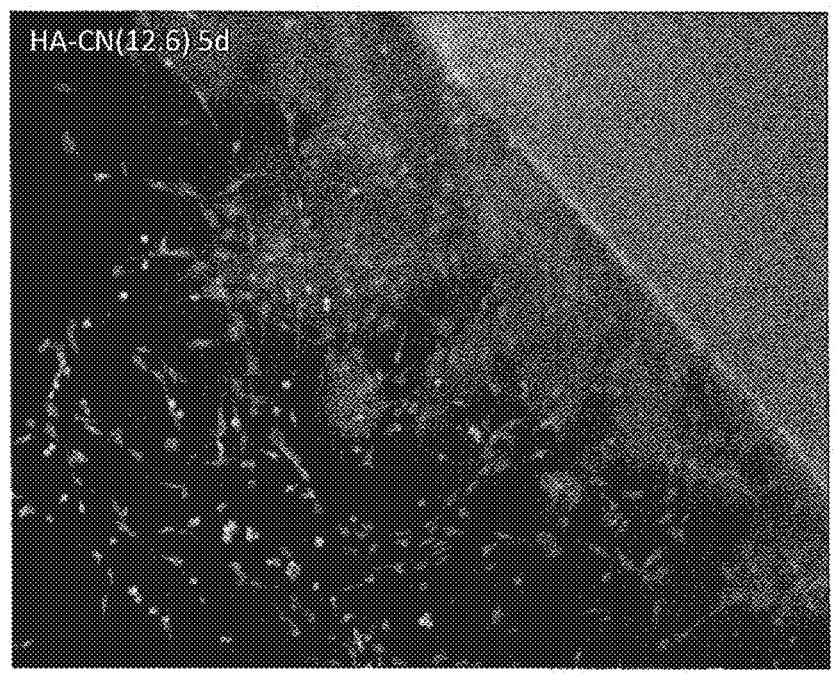
FIG. 2. is a bright field micrograph of cell migration from rat aortic rings for HA-collagen hydrogels of Example 10.

Hyaluronic Acid-Collagen(I) Hydrogels Support Human Endothelial and Fibroblast Cell Attachment and Outgrowth Samples of hyaluronic acid-collagen(I) matrices were tested for their ability to support cell attachment and outgrowth from rat aortic ring. Rat aorta were harvested and dissected into 2 mm×2 mm pieces and embedded in 50 µL gel in 96-well plates. The organ was cultured in endothelial cell growth medium with growth supplement (Lonza). Five days post culture, the culture was stained with live cell staining (Calcein AM). Few cells migrated out from HA(−) cultured rat aorta ring, however massive cell outgrowth of endothelial and fibroblasts occurred in collagen gel culture (FIG. 2).

Example 11

Figure 3A:
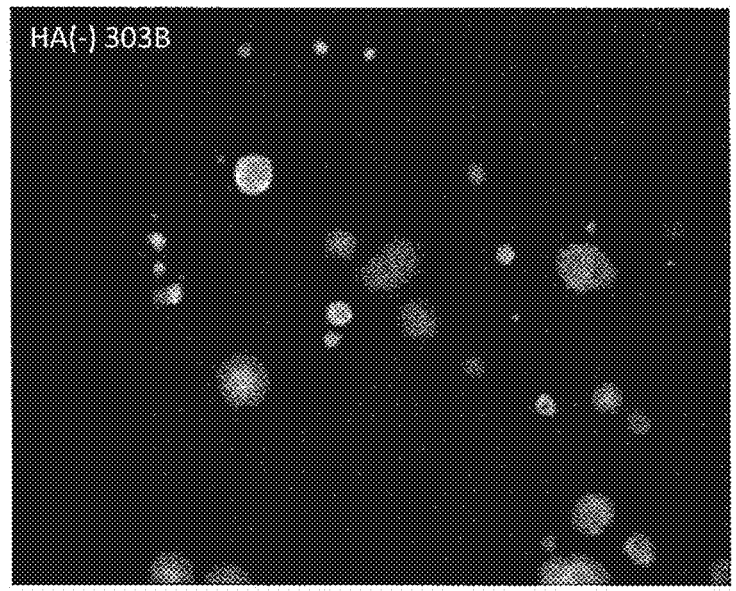
FIGS. 3A and 3B are bright field micrographs of the attachment and proliferation of HUVECs on hyaluronic acid-collagen(I) hydrogel according to Example 11 (FIG. 3B) as compared to a HA hydrogel control (FIG. 3A).
Figure 3B:
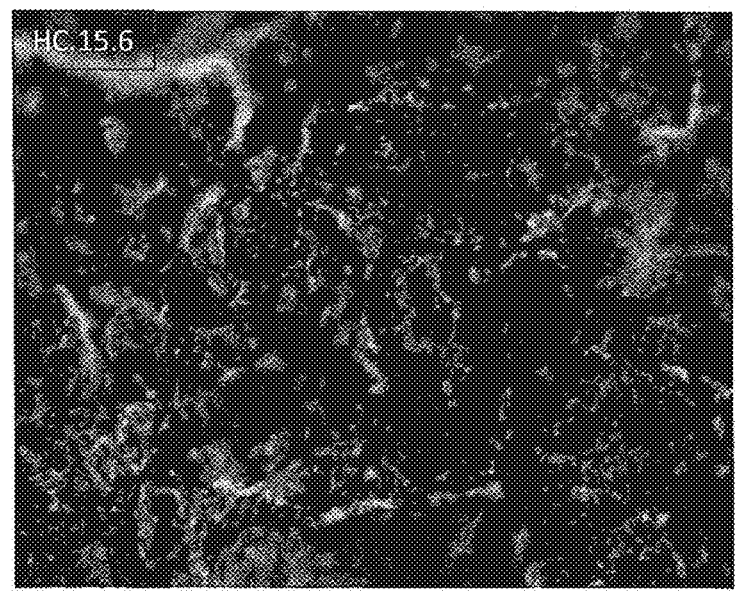

Hyaluronic Acid-Collagen(I) Hydrogels Support Human Endothelial Cell Proliferation Samples of hyaluronic acid-collagen(I) matrices were tested for their ability to support human umbilical vascular endothelial cell (HUVECs) proliferation. In 96-well plates, 50 µL gel beds were created in triplicate from the hyaluronic acid-collagen(I) hydrogels. Culture-expanded HUVECs (Lonza) were plated at 50,000 cells/cm² on the gel beds in endothelial cell growth medium with growth supplement (Lonza). The cells were cultured for up to 7 days at 37° C., 5% $CO_2$, after which live cell staining (Calcein AM) was performed. HUVECs proliferated very well on hyaluronic acid-collagen gels, but poorly on HA (−) gels. HUVECS attached to and propagated on hyaluronic acid-collagen gels (FIG. 3B), while on HA(−) gels, they did not attach, instead forming cellular aggregates (FIG. 3A).

Example 12

Enhanced Diffusion of Adipose Tissue-Specific and Pro-Angiogenic Growth Factors in Hyaluronic Acid-Human Collagen(I) Hydrogels Samples of hyaluronic acid-collagen(I) matrices from Example 8 were assessed for their ability to allow diffusion of pro-angiogenic (vascular endothelial growth factor, VEGF) and adipose tissue-specific growth factors (adiponectin, leptin). Improved diffusion to any or all of these growth factors would support the enhanced survival of co-grafted tissue, especially fat, since nutrient diffusion is a critical element to sustained tissue viability. To do this, 100 µL of each hydrogel tested was loaded into a 8 µm transwell (24 well plate) in order to make a gel column. Known concentrations of target factors were loaded on top of the gel, diluted in fibroblast basal medium (Cat#PCS-201-030, ATCC). Plates were allowed to incubate at 37° C. with 5% $CO_2$ in a tissue culture incubator, for 60 hours, thereby allowing the factors to diffuse through the gels. Diffusion of the specified factors through each hydrogel was measured by ELISA using the supernatant in the bottom chamber of the wells. Results indicated improved diffusion of the targeted factors compared to the reference, crosslinked hyaluronic acid (HA) hydrogel not containing collagen (Table 9).

TABLE 9

Hyaluronic acid-human collagen(I) hydrogels exhibit improved diffusion of adipokines

| Gel | Adiponectin (%) | Leptin (%) | VEGF (%) |
| --- | --- | --- | --- |
| HA(—) [control] | 100 ± 31 | 100 ± 21 | 100 ± 23 |
| HA-CN (16.8) | 200 ± 174 | 167 ± 28 | 119 ± 34 |
| HA-CN (3.3) | 211 ± 113 | 228 ± 6 | 178 ± 32 |
| HA-CN (12.6) | 106 ± 15 | 157 ± 14 | 119 ± 15 |
| HA-CN (12.12) | 108 ± 15 | 136 ± 4 | 103 ± 13 |
| HA-CN (24.12) | 189 ± 143 | 157 ± 54 | 112 ± 33 |

Note:
diffusion compared to the reference HA gel, lacking collagen type 1 [HA(—)].

Example 13

Hyaluronic Acid-Human Collagen(I) Hydrogels Stimulate Human Adipose Derived Stem Cell (hASCs) Secretion of Adipokines Samples of hyaluronic acid matrices with and without human collagen(I) were assayed for cellular leptin secretion following culture with hASCs. Leptin was used as a measure of differentiation into adipocytes in these three-dimensional cultures. For each sample, one million hASCs were encapsulated in 50 µL of hydrogel and cultured in a 0.4 µm transwell in a 24 well tissue culture plate. Cells were cultured using the StemPro Adipogenesis Differentiation Kit (Cat#A10070-01, Invitrogen) and were incubated at 37° C. with 5% $CO_2$ in a tissue culture incubator. Leptin levels in the media were measured by ELISA at 7, 14 and 21 days. The results in Table 10 indicate that hASCs cultured in HA-collagen(I) gels [HA-CN (16.8) and HA-CN (24.12)] released more leptin than cultures in HA gels lacking collagen(I) [HA(–).]

TABLE 10

Hyaluronic acid-human collagen(I) hydrogels stimulate leptin secretion in 3D culture.

| Sample ID | Day 7-Leptin (ng/mL) | Day 14-Leptin (ng/mL) | Day 21-Leptin (ng/mL) |
| --- | --- | --- | --- |
| HA-CN (16.8) | 1.144 ± 0.057 | 1.235 ± 0.020 | 1.270 ± 0.006 |
| HA-CN (24.12) | 1.057 ± 0.099 | 1.238 ± 0.019 | 1.262 ± 0.001 |
| HA(—) | 0.116 ± 0.013 | 0.261 ± 0.116 | 0.388 ± 0.046 |

Example 14

Hyaluronic Acid-Collagen(I) Hydrogels Improve Fat Graft Volume Retention

Samples of hyaluronic acid-collagen(I) from Example 8 were blended with human lipoaspirate (lipo) in a volume ratio of 2 parts lipo to 1 part gel, creating a lipo/gel graft. Control, lipo alone samples were used with the same lipo tissue volume as lipo/gel blends (0.66 mL). Lipo/gel grafts or lipo alone controls were implanted in a nude mouse model for evaluation of graft retention, gross tissue morphology, histologic cross sections and biomarkers for adipose tissue. Grafts were implanted as a bolus subcutaneously on the dorsum of female 6-week-old nude mice under anesthesia with two injections per mouse. One mL of each mixture was implanted through a small incision by 16 G cannula and the incision closed using surgical glue. A total of 14 injections of each material were made. Syringes were weighed before and after injection to determine the weight of injected material. After 6 weeks, the grafts were harvested for end-point assessment. Blending lipoaspirate with several formulations of hyaluronic acid-collagen(I) from Example 8 improved lipo/gel graft volume retention above lipoaspirate controls, in all, but one sample (A) (Table 11).

TABLE 11

Lipo/gel volume retention improvement compared to lipoaspirate study control at 6 weeks (difference in group means relative to lipo only control).

| Sample ID | [HA] (mg/mL) | [Col(I)] (mg/mL) | Improvement in Graft Volume (%) |
| --- | --- | --- | --- |
| A | 3 | 3 | −17 |
| B | 12 | 6 | 34 |
| C | 12 | 12 | 32 |
| D | 16 | 3 | 19 |
| E | 16 | 8 | 37 |
| F | 24 | 12 | 7 |
| G | 21 | 6 | 25 |

Moreover, lipo/gel grafts consistently showed improvements in volume retention across unique tissue donors and between distinct hydrogel lots. Four lots of 12 mg/mL hyaluronic acid—6 mg/mL collagen(I) were each blended with lipoaspirate tissue and showed improvements in graft retention ranging from 11% to 34% above lipoaspirate controls (Table 12).

TABLE 12

Improvement of lipoaspirate graft percent volume for four 12 mg/mL hyaluronic acid-6 mg/mL collagen(I) unique lots of material.

| Lot # | Tissue Donor | Improvement in Graft Volume (%) |
|---|---|---|
| 0131 | A | 11 |
| 0727 | B | 15 |
| 0811 | C | 22 |
| 0708 | D | 34 |

Example 15

Hyaluronic Acid-Collagen(I) Hydrogels Reduce the Variability in Retained Fat Graft Volume Samples of hyaluronic acid-collagen(I) from Example 8 were blended with human lipoaspirate (lipo) in a volume ratio of 2 parts lipo to 1 part gel, creating a lipo/gel graft. Control, lipo alone samples were used with the same lipo tissue volume as lipo/gel blends (0.66 mL). Lipo/gel grafts or lipo alone controls were implanted in a nude mouse model for evaluation of graft retention, gross tissue morphology, histologic cross sections and biomarkers for adipose tissue. Grafts were implanted as a bolus subcutaneously on the dorsum of female 6-week-old nude mice under anesthesia with two injections per mouse. One mL of each mixture was implanted through a small incision by 16 G cannula and the incision closed using surgical glue. A total of 14 injections of each material were made. Syringes were weighed before and after injection to determine the weight of injected material. After 6 weeks, the grafts were harvested for end-point assessment. Blending hyaluronic acid-collagen(I) with lipoaspirate reduced the variability in graft retention indicated by a reduction in the mean standard deviation compared to standard deviation of lipoaspirate controls (Table 13).

TABLE 13

Lipo/gel volume standard deviation compared to lipoaspirate study control at 6 weeks (difference in group deviation relative to lipo only control).

| Sample ID | [HA] (mg/mL) | [Col(I)] (mg/mL) | Reduction in Graft Variability (%) |
|---|---|---|---|
| A | 3 | 3 | 0 |
| B | 12 | 6 | −14 |
| C | 12 | 12 | −17 |
| D | 16 | 3 | −4 |
| E | 16 | 8 | −16 |
| F | 24 | 12 | 0 |
| G | 21 | 6 | −4 |

Example 16

Hyaluronic Acid-Collagen(I) Hydrogels Improve Fat Graft Survival and Tissue Morphology Samples of hyaluronic acid-collagen(I) from Example 8 were blended with human lipoaspirate (lipo) in a volume ratio of 2 parts lipo to 1 part gel, creating a lipo/gel graft. Lipo/gel grafts were implanted in a nude mouse model for evaluation of graft retention, gross tissue morphology, histologic cross sections and biomarkers for adipose tissue. Grafts were implanted as a bolus subcutaneously on the dorsum of female 6-week-old nude mice under anesthesia with two injections per mouse. One mL of each mixture was implanted through a small incision by 16 G cannula and the incision closed using surgical glue. A total of 14 injections of each material were made. Syringes were weighed before and after injection to determine the weight of injected material. After 6 weeks, the grafts were harvested for histologic end-point assessment. Blending hyaluronic acid-collagen(I) with lipoaspirate improved fat graft survival and tissue morphology as represented through hematoxylin & eosin staining of paraffin embedded, formalin fixed sections cut throughout the fat/gel graft (FIGS. 4A-4D).

Figure 4A:
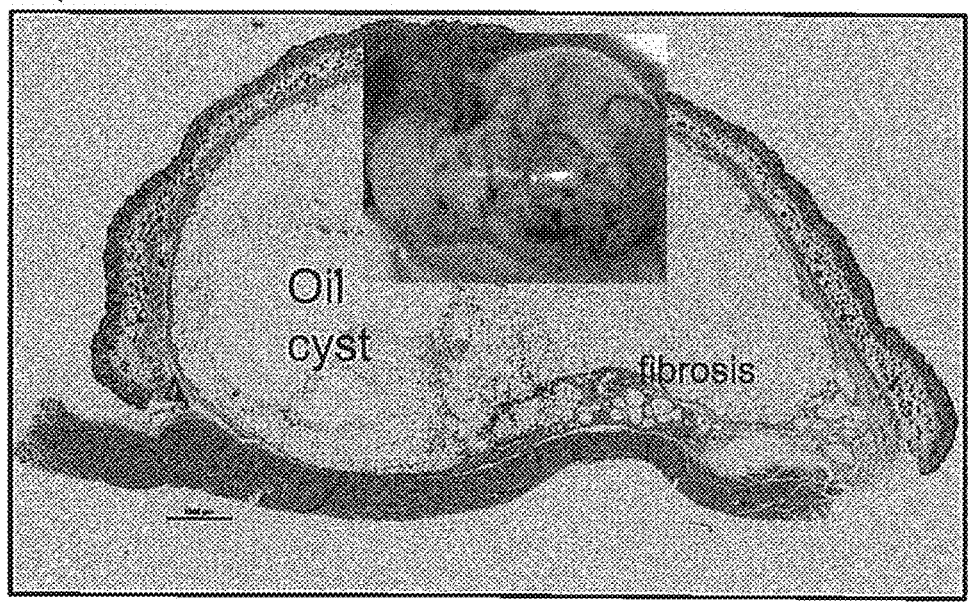
FIGS. 4A through 4D show photographs as insets and corresponding H&E micrographs of lipoaspirate/hyaluronic acid-collagen(I) hydrogel grafts according to Example 16 (FIGS. 4B, 4C, and 4D) as compared to grafts of lipoaspirate only (FIG. 4A).
Figure 4B:
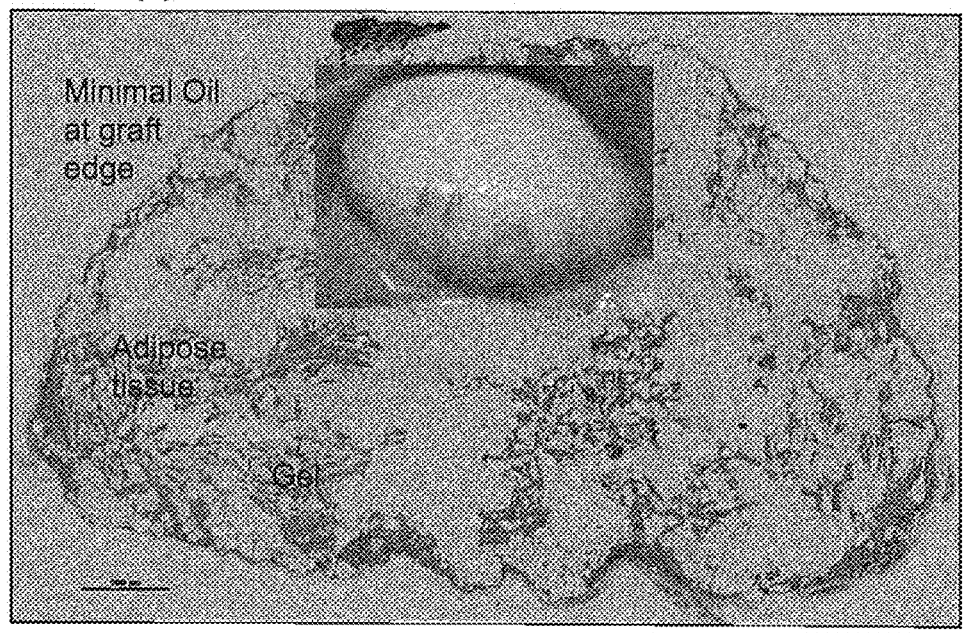
Figure 4C:
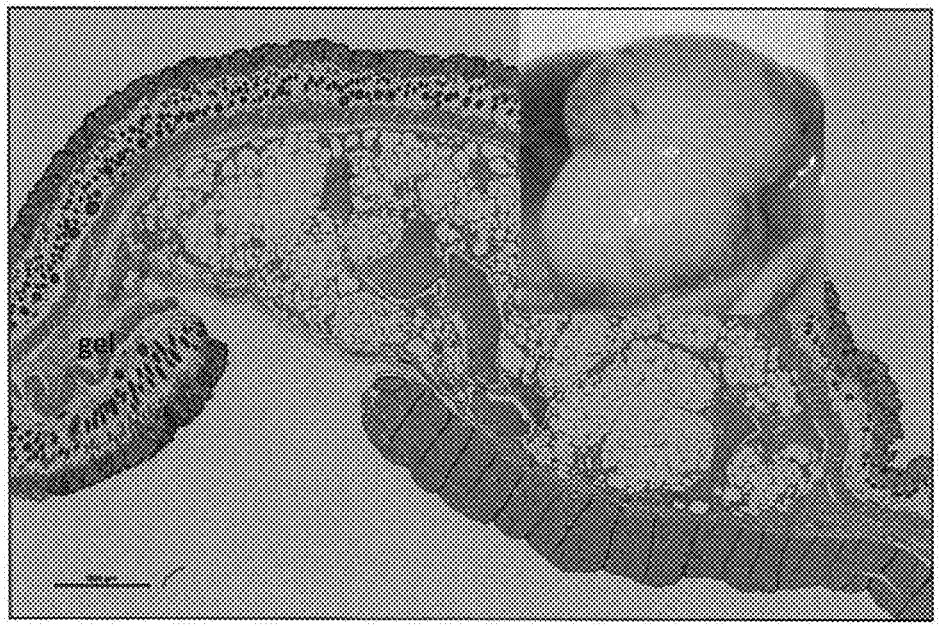
Figure 4D:
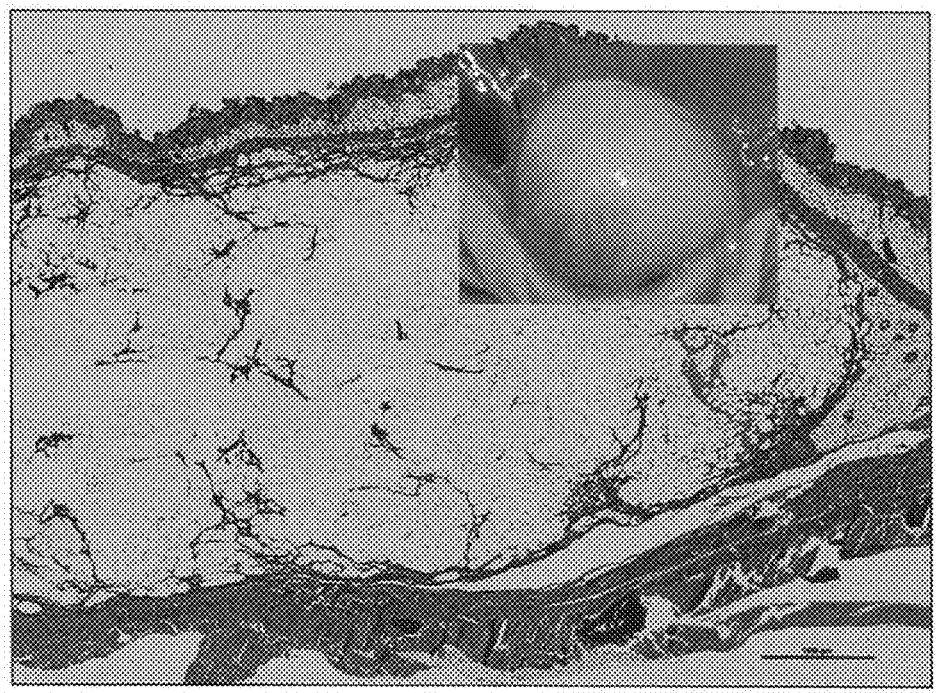

Turning to FIGS. 4A-4D, photographs of lipo/gel explants are provided as insets along with corresponding H&E micrographs. Gross examination of explanted gel samples indicated signs of reduced fibrosis and oil cysts, and increased tissue integrity in several gel formulations (FIGS. 4B-4D) compared with control (FIG. 4A).

Example 17

Enhanced Angiogenesis in Fat Grafts Blended with Hyaluronic Acid-Collagen(I) Hydrogels Samples of hyaluronic acid-collagen(I) were implanted in a nude mouse model for evaluation of angiogenic potential. Gels were implanted as a bolus subcutaneously on the dorsum of female 6-week-old nude mice under anesthesia with two injections per mouse. Lipo was mixed with hydrogels at a ratio of 2 parts lipo to 1 part gel (total 1 mL). Animals receiving lipo alone were used as controls (0.66 mL total fat injected). Six weeks post implantation, fat grafts were explanted and a subset used to assess angiogenesis levels by real-time PCR. Fat grafts used for real-time PCR were placed in RNALater (Ambion) to protect RNA from degradation immediately after being explanted. The RNALater treated tissue samples were lyophilized and pulverized before being used for RNA isolation. Total RNA was isolated (Aurum Total RNA Fatty and Fibrous kit, Bio-Rad) and its quality and quantity were assessed by Nanodrop and 1 agarose gel. The SuperScript VILO cDNA Synthesis kit (Invitrogen) was used for cDNA synthesis. The overall levels of angiogenesis were evaluated by CD31, an endothelial cell surface marker, gene expression levels by Taqman gene expression assay (Invitrogen) with StepOne Plus equipment and Gene expression Analysis Software (Invitrogen). Human CD31 expression in grafts with HA-Col(I) gels showed significantly higher levels than lipoaspirate alone, more than 3 fold elevation (expression fold change, Table 14), consistent with the previous finding that hyaluronic acid-collagen(I) hydrogels support endothelial cell survival and proliferation in vitro.

TABLE 14

Human CD31 (PECAM) gene expression in fat grafts with and without HA-collagen(I)

| Sample (human CD31 gene) | N | Mean Expression Fold Change Relative to Lipo alone |
|---|---|---|
| Lipo alone | 5 | 1.00 ± 0.71 |
| Lipo + HA-CN1 | 5 | 3.16 ± 0.55 |

Example 18

Enhanced Adipogenic Gene Expression in Fat Grafts Blended with Hyaluronic Acid-Collagen(I) Hydrogels Samples of hyaluronic acid-collagen(I) were implanted in a nude mouse model for evaluation of adipogenic potential.

Gels were implanted as a bolus subcutaneously on the dorsum of female 6-week-old nude mice under anesthesia with two injections per mouse. Lipo was mixed with hydrogels at a ratio of 2 parts lipo to 1 part gel (total 1 mL). Animals receiving lipo alone were used as controls (0.66 mL total fat injected). Six weeks post implantation, fat grafts were explanted and a subset used to assess adipogenesis levels by real-time PCR. Fat grafts used for real-time PCR were placed in RNALater (Ambion) to protect RNA from degradation immediately after being explanted. The RNALater treated tissue samples were lyophilized and pulverized before being used for RNA isolation. Total RNA was isolated (Aurum Total RNA Fatty and Fibrous kit, Bio-Rad) and its quality and quantity were assessed by Nanodrop and 1 agarose gel. The SuperScript VILO cDNA Synthesis kit (Invitrogen) was used for cDNA synthesis. The overall adipogenesis levels of the fat grafts were evaluated using adipocyte specific gene, leptin, expression at the RNA level. Grafts with HA-Col(I) gels showed a 2.5 fold increase in leptin gene expression over the lipo alone samples (Table 15, $p<0.05$), suggesting an enhancement in adipogenic gene expression.

TABLE 15

Leptin gene expression in fat grafts with and without HA-collagen(I)

| Sample (human leptin gene) | N | Mean Expression Fold Change Relative to Lipo alone |
|---|---|---|
| Lipo alone | 4 | 1.00 ± 0.76 |
| Lipo + HA-CN1 | 5 | 2.53 ± 1.00 |

Example 19

Reduced Inflammation in Fat Grafts Blended with Hyaluronic Acid-Collagen(I) Hydrogels Samples of hyaluronic acid-collagen(I) were implanted in a nude mouse model to evaluate the level of inflammation associated with these gels. Gels were implanted as a bolus subcutaneously on the dorsum of female 6-week-old nude mice under anesthesia with two injections per mouse. Lipo was mixed with hydrogels at a ratio of 2 parts lipo to 1 part gel (total 1 mL). Animals receiving lipo alone were used as controls (0.66 mL total fat injected). Six weeks post implantation, fat grafts were explanted and a subset used to assess general inflammation levels by real-time PCR. Fat grafts used for real-time PCR were placed in RNALater (Ambion) to protect RNA from degradation immediately after being explanted. The RNALater treated tissue samples were lyophilized and pulverized before being used for RNA isolation. Total RNA was isolated (Aurum Total RNA Fatty and Fibrous kit, Bio-Rad) and its quality and quantity were assessed by Nanodrop and 1% agarose gel. The SuperScript VILO cDNA Synthesis kit (Invitrogen) was used for cDNA synthesis.

The inflammatory responses of fat and gel grafts were determined by the expression level of three genes, CD68 (a general macrophage marker), CD11c (a marker for macrophages involved in M1 pro-inflammatory pathway), and CD163 (a marker for macrophages involved in M2 anti-inflammatory pathway). The CD68 positive macrophage response represents total macrophages and overall macrophage related inflammatory responses. Tissue macrophages, however, can exist in different activation states: either pro-inflammatory classically activated by interferon-γ or lipopolysaccharide, known as M1, or anti-inflammatory alternatively activated by IL-13 or IL-4, known as M2. Depending on microenvironmental stimuli, M1- and M2-activated macrophages fulfill different functions through the production of pro- or anti-inflammatory factors. M2 macrophage activation is known to be involved in repair and remodeling of tissues, and as such, represents a productive response to the injection or implantation of a biomaterial.

The results of real-time PCR indicated that fat grafts containing HA-CN1 exhibited reduced levels of CD68 (<2 fold) compared to lipo alone grafts. While also not significant, the reduced expression of CD11c and higher CD163 expression levels (Table 16), suggest that HA-CN1 might have some effects in reducing pro-inflammatory responses and enhancing anti-inflammatory responses. Importantly, CD68 expression in fat grafts containing HA-CN1 were not elevated, compared to lipo alone controls, suggesting that the hydrogel itself was not augmenting any inflammatory response associated with the grafting of tissue.

TABLE 16

CD68, CD11c, and CD163 gene expression in fat grafts with and without HA-collagen(I)

| Mean Expression Fold Change Relative to Lipo alone | N | mouse CD68 | mouse CD11c | mouse CD163 |
|---|---|---|---|---|
| Lipo alone | 5 | 1 ± 0.23 | 1 ± 0.31 | 1 ± 0.25 |
| Lipo + HA-CN1 | 5 | 0.69 ± 0.23 | 0.62 ± 0.20 | 1.29 ± 0.34 |

Example 20

Adipose Tissue Transplant for Breast Defect Correction

This example illustrates the use of compositions and methods disclosed herein for a breast defect correction.

A 32-year-old woman presented with complaints that the medial portions of her breast implants were visible, which accentuated the "bony" appearance of her sternum. In addition, she felt her breasts were too far apart. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. The harvested area is injected subcutaneously with a standard tumescent fluid solution containing a saline solution, 0.5% lidocaine, and about 0.001% epinephrine. Using an 11-blade scalpel, a small puncture wound is made in order to transverse the dermis. The blade is turned 360 degrees to complete the wound. A two-holed blunt harvesting cannula (3 mm inner diameter) connected to a vacuum pump at low negative pressure (0.5 atm) is then inserted into the subcutaneous adipose tissue plane. The cannula is then moved throughout the plane to disrupt the connective tissue architecture. The volume of aspirate obtained is about 300 mL. The harvest adipose tissue is processed by centrifugation at 3,000 g for 3 minutes to separate health adipocytes and regenerative cells from blood, infiltration fluid and cell debris.

A hyaluronic acid-collagen(I) gel, such as described in Example 1, is mixed with the processed adipose tissue. The amount of compound added is an amount sufficient to promote formation of a blood supply sufficient to support the transplanted tissue. This composition is then transferred to 3 mL syringes. One-holed blunt infiltration cannulas (3 mm inner diameter) are used to place the adipose tissue subcutaneously over the lateral sternum and medial breast bilaterally, 70 mL on the right and 50 mL on the left. The adipose tissue is administered in a tear like fashion to increase the surface area to volume ratio.

Alternatively, the adipose tissue is first administered into the individual, and a hyaluronic acid-collagen(I) gel, such as described in Example 1, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure. Approximately six months after the procedure, the soft tissue replacement appears to be stable and the breast volume has not decreased to any noticeable degree.

Example 21

Adipose Tissue Transplant for Breast Augmentation

This example illustrates the use of compositions and methods disclosed herein for a breast augmentation.

A 28-year-old woman presented micromastia or breast hypoplasia. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. Using a 10-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 600 mL. The harvest adipose tissue is processed by centrifugation at 2,700 g for 5 minutes to separate healthy adipocytes and regenerative cells from blood, infiltration fluid and cell debris. The centrifuged adipose tissue is then washed once is a Ringer's saline solution with lactone.

A hyaluronic acid-collagen(I) gel, such as described in Example 1, is mixed with the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place the adipose tissue subcutaneously using axillary, periareolar, and inframammary routes bilaterally, 190 mL on the right and 245 mL on the left. The adipose tissue is administered in a tear like fashion to increase the surface area to volume ratio.

Alternatively, the adipose tissue is first administered into the individual, and a hyaluronic acid-collagen(I) gel, such as described in Example 1, is subsequently administered into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure.

Example 22

Adipose Tissue Transplant for Breast Disorder

This example illustrates the use of compositions and methods disclosed herein for a breast disorder.

A 49-year-old woman presented with bilaterial tuberous breast deformity. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the abdomen, buttock, lateral and medial thigh, and trochanter regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 1,400 mL.

The harvested adipose tissue is divided into two, approximately equal portions. One portion is processed by gravity sedimentation to separate healthy adipocytes and regenerative cells from blood, infiltration fluid and cell debris. The other portion is used to isolate regenerative cells. This portion is digested with 0.075% collagenase in buffered saline for 30 minutes on a shaker at 37° C. Regenerative cells are then separated from mature adipocytes and connective tissue by centrifuging at 800 g for 10 minutes. The pellet containing the regenerative cells is then washed three times with buffered saline. The washed regenerative cells are then added back to the sediment purified adipose tissue.

A hyaluronic acid-collagen(III) gel made in accordance with methods described herein, is mixed with the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place the adipose tissue subcutaneously in multiple planes axillary, periareolar, and inframammary routes bilaterally, 380 mL on the right and 370 mL on the left. The adipose tissue is administered in a tear like fashion to increase the surface area to volume ratio.

The individual is monitored for approximately 21 days. The physician evaluates the engrafted tissue and determines that the engraftment was successful. Both the woman and her physician are satisfied with the results of the procedure.

Approximately twelve months after the procedure, the woman indicates that her quality of life has improved.

In another instance, the individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 23

Adipose Tissue Transplant to Treat Stress Urinary Incontinence

This example illustrates the use of compositions and methods disclosed herein for treating stress urinary incontinence.

A 55 year old man presents with urinary incontinence. Pre-operative evaluation of the patient includes routine history and physical examination in addition to thorough informed consent disclosing all relevant risks and benefits of the procedure. The physician evaluating the individual determines that he is a candidate for a soft tissue replacement method using the compositions and methods disclosed herein.

To begin the procedure, adipose tissue is harvested from the man. The procedure is performed at the individual's bedside. The physician examines the individual's habitus for a suitable site or sites to harvest adipose tissue and selects the abdomen, and lateral and medial thigh regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 900 mL.

A hyaluronic acid-collagen(I) gel, such as described in Example 1, is mixed with the processed adipose tissue. The amount of compound added is an amount sufficient to promote formation of a blood supply sufficient to support the transplanted tissue. This composition is then transferred to 20 mL syringes. One-holed blunt infiltration cannulas (14-gauge) are used to place about 800 mL of adipose tissue transdermally into the bladder neck and proximal urethra regions.

Alternatively, the adipose tissue is first administered into the individual, and A hyaluronic acid-collagen(I) gel, such as described in Example 1, is subsequently administered into the same, or in the vicinity of, the region where the adipose tissue was implanted.

The individual is monitored after the procedure. Approximately three days after the transplant, he experiences a decreased frequency of incontinence. Approximately one month after the procedure, the individual indicates that his quality of life has improved. The physician evaluates the engrafted tissue and determines that the long-term engraftment was successful.

Example 24

Adipose Tissue Transplant for Breast Defect Correction

This example illustrates the use of compositions and methods disclosed herein for a breast defect correction.

A 56-year-old woman presents with a surgically removed breast due to cancer. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, a breast mound is formed using a TRAM-flap procedure. In this procedure, a portion of abdomen tissue, including skin, adipose tissue, minor muscles and connective tissues, is taken from the patient's abdomen and transplanted onto the breast site. This tissue is then used to create a breast mound.

A hyaluronic acid-collagen(III) gel, such as described herein, is then administered into the breast mound region. The amount of compound administered is an amount sufficient to promote formation of a blood supply sufficient to support the transplanted tissue.

The individual is monitored for approximately 21 days. The physician evaluates the engrafted tissue and determines that the engraftment was successful. Both the woman and her physician are satisfied with the results of the procedure. Approximately one month after the procedure, the woman indicates that her quality of life has improved. Subsequent surgery is performed to create a nipple and areola.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the," and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of grafting fat in a human subject, the method comprising administering a composition to a soft tissue of the subject, wherein the composition comprises:
   (i) a hydrogel comprising:
      (a) water; and
      (b) a crosslinked macromolecular matrix comprising hyaluronic acid crosslinked to collagen via a plurality of crosslink units, wherein at least a portion of the crosslink units comprise an amide bond; and the crosslinked macromolecular matrix has a weight ratio of the hyaluronic acid to the collagen of 1:1 to 7:1;
   wherein said hydrogel has a hyaluronic acid concentration of 6 mg/mL to 21 mg/mL, a collagen concentration of 3 mg/mL to 12 mg/mL, and a storage modulus value of between 850 Pa and 5,000 Pa; and
   (ii) a fat component, comprising adipose tissue, adipocytes, or both, wherein the fat component has been explanted from the human subject;
   thereby increasing the volume of fat in the soft tissue of the subject.

2. The method of claim 1, wherein the administration of the composition results in an increase in fat graft volume retention as compared to administering the fat component alone.

3. The method of claim 2, wherein the administration of the composition reduces variability in the retained fat graft volume as compared to administering the fat component alone.

4. The method of claim 1, wherein the hyaluronic acid is crosslinked to the collagen using a coupling agent which is not part of the crosslink unit.

5. The method of claim 1, wherein the composition has a fat: hydrogel weight ratio of 1:1 to 5:1.

6. The method of claim 1, wherein the hydrogel has a storage modulus value of between 1,000 Pa and 4,000 Pa.

7. The method of claim 1, wherein the crosslinked macromolecular matrix has a weight ratio of the hyaluronic acid to the collagen of 1:1 to 2:1.

8. The method of claim 1, wherein the hydrogel has a collagen concentration of greater than or equal to 6 mg/mL.

9. The method of claim 1, wherein the hydrogel has a hyaluronic acid concentration of at least 9 mg/mL.

10. The method of claim 1, wherein the hydrogel has a collagen concentration of 6 mg/mL, 8 mg/mL or 12 mg/mL.

11. The method of claim 1, wherein the hydrogel has a hyaluronic acid concentration of 12 mg/mL and a collagen concentration of 6 mg/mL.

12. The method of claim 1, wherein the hydrogel has a hyaluronic acid concentration of 12 mg/mL and a collagen concentration of 12 mg/mL.

13. The method of claim 1, wherein the hydrogel has a hyaluronic acid concentration of 16 mg/mL and a collagen concentration of 8 mg/mL.

14. The method of claim 1, wherein the hydrogel has a hyaluronic acid concentration of at least 9 mg/mL and a collagen concentration of greater than or equal to 6 mg/m L.

15. The method of claim 1, wherein the hyaluronic acid is crosslinked to the collagen using hyaluronic acid having a molecular weight of 1,000,000 to 5,000,000 daltons.

16. The method of claim 1, wherein the hyaluronic acid is crosslinked to the collagen using hyaluronic acid having a molecular weight of 1,000,000 daltons to 3,000,000 daltons.

17. The method of claim 1, wherein the collagen is porcine or human collagen type I.

18. The method of claim 1, wherein the administering comprises injecting or implanting the composition into the soft tissue of the subject.

19. The method of claim 1, wherein the fat component contains adipocytes, and wherein the administration of the composition enhances adipocyte proliferation as compared to administering adipocytes alone.

20. The method of claim 1, wherein the fat component contains adipose tissue, and wherein the administration of the composition enhances adipose tissue growth as compared to administering adipose tissue alone.

21. A method of grafting fat in a soft tissue of a human subject, the method comprising:
   (i) injecting a hydrogel component into the soft tissue of the subject, wherein the hydrogel component comprises:
      (a) water; and
      (b) a crosslinked macromolecular matrix comprising hyaluronic acid crosslinked to collagen via a plurality of crosslink units, wherein at least a portion of the crosslink units comprise an amide bond; and the crosslinked macromolecular matrix has a weight ratio of the hyaluronic acid to the collagen of 1:1 to 7:1;
   wherein said hydrogel component has a hyaluronic acid concentration of 6 mg/mL to 21 mg/mL, a collagen concentration of 3 mg/mL to 12 mg/mL, and a storage modulus value of between 850 Pa and 5,000 Pa; and
   (ii) administering a fat component to the soft tissue of the subject, wherein the fat component contains adipose tissue, adipocytes, or both, and wherein the fat component has been explanted from the human subject;
   thereby increasing the volume of fat in the soft tissue of the subject.

22. The method of claim 21, wherein the injection of the hydrogel component and the administration of the fat component to the soft tissue is performed sequentially.

23. The method of claim 22, wherein the injection of the hydrogel component to the soft tissue precedes the administration of the fat component to the soft tissue.

24. The method of claim 21, wherein the fat component is injected into the soft tissue.

25. The method of claim 24, wherein the hydrogel component is contacted with the fat component prior to the injection to provide a single composition, which is injected into the soft tissue of the subject.

26. The method of claim 25, wherein the composition has a fat:hydrogel weight ratio of 1:1 to 5:1.

27. The method of claim 21, wherein fat graft volume retention is increased as compared to administering the fat component alone.

28. The method of claim 27, wherein variability in the retained fat graft volume is reduced as compared to administering the fat component alone.

29. The method of claim 21, wherein the hyaluronic acid is crosslinked to the collagen using a coupling agent which is not part of the crosslink unit.

30. The method of claim 21, wherein the hydrogel component has a storage modulus value of between 1,000 Pa and 4,000 Pa.

31. The method of claim 21, wherein the crosslinked macromolecular matrix has a weight ratio of the hyaluronic acid to the collagen of 1:1 to 2:1.

32. The method of claim 21, wherein the hydrogel component has a collagen concentration of greater than or equal to 6 mg/mL.

33. The method of claim 21, wherein the hydrogel component has a hyaluronic acid concentration of at least 9 mg/mL.

34. The method of claim 21, wherein the hydrogel component has a collagen concentration of 6 mg/mL, 8 mg/mL or 12 mg/mL.

35. The method of claim 21, wherein the hydrogel component has a hyaluronic acid concentration of 12 mg/mL and a collagen concentration of 6 mg/mL.

36. The method of claim 21, wherein the hydrogel component has a hyaluronic acid concentration of 12 mg/mL and a collagen concentration of 12 mg/mL.

37. The method of claim 21, wherein the hydrogel component has a hyaluronic acid concentration of 16 mg/mL and a collagen concentration of 8 mg/mL.

38. The method of claim 21, wherein the hydrogel component has a hyaluronic acid concentration of at least 9 mg/mL and a collagen concentration of greater than or equal to 6 mg/mL.

39. The method of claim 21, wherein the hyaluronic acid is crosslinked to the collagen using hyaluronic acid having a molecular weight of 1,000,000 to 5,000,000 daltons.

40. The method of claim 21, wherein the hyaluronic acid is crosslinked to the collagen using hyaluronic acid having a molecular weight of 1,000,000 daltons to 3,000,000 daltons.

41. The method of claim 21, wherein the collagen is porcine or human collagen type I.

42. The method of claim 21, wherein adipocyte proliferation is enhanced as compared to administering adipocytes alone.

43. The method of claim 21, wherein adipose tissue growth is enhanced as compared to administering adipose tissue alone.

* * * * *